United States Patent
Duncan et al.

(10) Patent No.: US 10,272,126 B2
(45) Date of Patent: Apr. 30, 2019

(54) NANOPARTICLE-STABILIZED MICROCAPSULES, DISPERSIONS COMPRISING NANOPARTICLE-STABILIZED MICROCAPSULES, AND METHOD FOR THE TREATMENT OF BACTERIAL BIOFILMS

(71) Applicant: The University of Massachusetts, Boston, MA (US)

(72) Inventors: Bradley Duncan, Andover, MA (US); Xiaoning Li, Hillsboro, OR (US); Vincent M. Rotello, Amherst, MA (US)

(73) Assignee: THE UNIVERSITY OF MASSACHUSETTS, Boston, MA (US)

( * ) Notice: Subject to any disclaimer, the term of this patent is extended or adjusted under 35 U.S.C. 154(b) by 45 days.

(21) Appl. No.: 15/216,134

(22) Filed: Jul. 21, 2016

(65) Prior Publication Data

US 2017/0049113 A1    Feb. 23, 2017

Related U.S. Application Data

(60) Provisional application No. 62/208,114, filed on Aug. 21, 2015.

(51) Int. Cl.
| | |
|---|---|
| *A01N 65/22* | (2009.01) |
| *A01N 25/04* | (2006.01) |
| *A01N 31/04* | (2006.01) |
| *A61L 2/18* | (2006.01) |
| *A61K 9/107* | (2006.01) |
| *A61K 31/12* | (2006.01) |
| *A61K 36/534* | (2006.01) |
| *A01N 25/22* | (2006.01) |
| *A61K 9/50* | (2006.01) |
| *A01N 25/28* | (2006.01) |
| *A01N 35/02* | (2006.01) |
| *A61L 2/00* | (2006.01) |
| *A61K 47/52* | (2017.01) |

(52) U.S. Cl.
CPC ........... *A61K 36/534* (2013.01); *A01N 25/04* (2013.01); *A01N 25/28* (2013.01); *A01N 35/02* (2013.01); *A61K 9/501* (2013.01); *A61K 31/12* (2013.01); *A61K 47/52* (2017.08); *A61L 2/0082* (2013.01); *Y02A 50/473* (2018.01); *Y02A 50/478* (2018.01); *Y02A 50/479* (2018.01)

(58) Field of Classification Search
CPC ........ A01N 65/22; A01N 25/04; A01N 31/04; A61N 25/22; A61K 47/48015; A61K 9/107; A61K 31/12; A61K 36/534; A61L 2/18; A61L 2202/21; A61L 2202/24

See application file for complete search history.

(56) References Cited

U.S. PATENT DOCUMENTS

| | | | |
|---|---|---|---|
| 5,051,305 A | 9/1991 | Whitaker, Sr. | |
| 2013/0101545 A1* | 4/2013 | Pluyter | C07C 205/44 424/76.1 |
| 2014/0044760 A1* | 2/2014 | Lei | B01J 13/18 424/401 |
| 2014/0193350 A1* | 7/2014 | Bauer | A61K 8/347 424/70.11 |

FOREIGN PATENT DOCUMENTS

| | | | | |
|---|---|---|---|---|
| JP | WO 2015016368 A1 * | 2/2015 | | B01J 13/14 |
| WO | 2009063257 A2 | 5/2009 | | |

OTHER PUBLICATIONS

Binks et al (Published: 2010). Phys. Chem. Chem. Phys., 12: 11954-11966.*
Zhao et al. "Microencapsulation of Hydrophobic Liquids in Closed All-Silica Colloidsomes." Langmuir, Apr. 1, 2014, (30): 4253-4262.*
Soto-Cantu et al. "Synthesis and Rapid Characterization of Amine-Functionalized Silica." Langmuir, Mar. 20, 2012, (28): 5562-5569.*
Ribeiro et al. "Functional Films from Silica/Polymer Nanoparticles." Materials, May 15, 2014, (7): 3881-3900.*
Binks,; "Similarities and Differences. Curr. Opin." Colloid Interface Sci.;2002;7:21-41.
Burt, "Essential Oils: Theit antibacterial properties and potential applications in foods—a review";International Journal of Food Microbiology;2004;94:223-253.
Busscher et al.; "Biofilm Formation on Dental Restorative and Implant Materials." J. Dent. Res.;2010;89:657-665.
Carpenter et al.; "Dual Action Antimicrobials: Nitric Oxide Release from Quaternary Ammonium-Functionalized Silica Nanoparticles." Biomacromolecules; 2012;13:3334-3342.
Chang et al.; "Physicochemical Properties and Antimicrobial Efficacy of Carvacrol Nanoemulsions Formed by Spontaneous Emulsification." J. Agric. Food Chem.;2013;61:8906-8913.
Chen et al.; "Impacts of Sample Preparation Methods on Solubility and Antilisterial Characteristics of Essential Oil Components in Milk." Appl. Environ. Microbiol.;2014;80:907-916.
Costerton et al.; "The Application of Biofilm Science to the Study and Control of Chronic Bacterial Infections." J. Clin. Invest;2003;112:1466-1477.
Costerton et al.;"Biofilm in Implant Infections: Its Production and Regulation.";Int. J. Artif. Organs; 2005;28:1062-1068.
Costerton et al; "Bacterial Biofilms: A Common Cause of Persistent Infections."; Science; 1999; 284: 1318-1322.

(Continued)

*Primary Examiner* — Doan T Phan
(74) *Attorney, Agent, or Firm* — Cantor Colburn LLP

(57) ABSTRACT

A stabilized microcapsule includes a liquid hydrophobic core including an essential oil and an aromatic monoaldehyde, and a shell encapsulating the core, the shell including a plurality of amino-functionalized inorganic nanoparticles. Also disclosed is a dispersion including a plurality of the stabilized microcapsules. The microcapsules and dispersions can be particularly useful for treating a bacterial biofilm.

16 Claims, 14 Drawing Sheets

(56) References Cited

OTHER PUBLICATIONS

Decker, et al., "Quick and Simple Method for the Quantitation of Lactate Dehydrogenase Release in Measurements of Cellular Cytotoxicity and Tumor Necrosis Factor (TNF) Activity", J. Immunol. Methods 1988, 115, 61-69.
Duncan et al."Nanoparticle-Stabilized Capsules for the Treatment of Bacterial Biofilms", American Chemical Society, Published online., 10.1021/ACSnao.5b01696; Accepted Jun. 17, 2015; A-H.
Duncan et al.,"Hybrid Organic-Inorganic Colloidal Composites 'Sponges' via Inmternal Crosslink"; Small;2015;11:1302-1309.
Ehrlich et al.; "Mucosal Biofilm Formation on Middle-Ear Mucosa in the Chinchilla Model of Otitis Media." JAMA; 2002;287:1710.
Ghouchi, et al,; "Nanoparticle Coated Submicron Emulsions: Sustained in-Vitro Release and Improved Dermal Delivery of All-Trans-Retinol." Pharm. Res.; 2009;26:1764-1775.
Gomes, et al."Poly (DL-lactide-co-glycolide) (PLGA) Nanoparticles with Entrapped trans-Cinnanaldehyde and Eugenol for Antimicrobial Delivery Applications"; Journal of Food Science;2011;76:N16-N24.
Goswami et al.; "Biocompatible Nanocarrier Fortified with a Dipyridinium-Based Amphiphile for Eradication of Biofilm." ACS Appl. Mater. Interfaces;2014;6:16384-16394.
Harrison et al.; Multimetal Resistance and Tolerance in Microbial Biofilms.: Nat. Rev. Microbiol.; 2007;5:928-938.
Hemaiswarya et al.' "Synergism between Natural Products and Antibiotics against Infectious Diseases." Phytomedicine; 2008;15:639-652.
Hurdle et al.; "Targeting Bacterial Membrane Function: An Underexploited Mechanism for Treating Persistent Infections." Nat. Rev. Microbiol.;2011;9:62-75.
James et al.; "Biofilms in Chronic Wounds. Wound Repair Regen." 2007;16:37-44.
Kalemba, et al., "Antibacterial and Antifungal Properties of Essential Oils", Curr. Med. Chem. 2003, 10, 813-829.
Kavanaugh et al.;"Selected Antimicrobial Essential Oils Eradicate *Pseudomonas* Spp. and *Staphylococcus aureus* Biofilms." Appl. Environ. Microbiol.;2012;78:4057-4061.
Labouta et al. "Interaction of Inorganic Nanoparticles with the Skin Barrier: Current Status and Critical Review." Nanomedicine: Nanotechnology, Biology, and Medicine;2013;9,:9-54.
Levy et al.; "Antibacterial Resistance Worldwide: Causes, Challenges and Responses." Nat. Med.; 2004;10:S122-S129.
Li et al.; "Rapid Identification of Bacterial Biofilms and Biofilm Wound Models Using a Multichannel Nanosensor." ACS Nano; 2014;8:12014-12019.
Li et al.; Control of Nanoparticle Penetration into Biofilms through Surface Design.; Chem. Commun. (Camb).;2015;51:282-285.
Liang et al. "Physical and Antimicrobial Properties of Peppermint Oil Nanoemulsions." J. Agric. Food Chem.;2012;60:7548-7555.
Lindsay et al, "Bacterial Biofilms within the Clinical Setting: What Healthcare Professionals Should Know." J. Hosp. Infect;2006;64:313-325.
Lynch et al.;"Bacterial and Fungal Biofilm Infections." Annu. Rev. Med.;2008;59:415-428.
Marion-Ferey et al.; "Biofilm Removal from Silicone Tubing: An Assessment of the Efficacy of Dialysis Machine Decontamination Procedures Using an in Vitro Model." J. Hosp. Infect.;2003;53:64-71.
Nabeshi et al.; "Systemic Distribution, Nuclear Entry and Cytotoxicity of Amorphous Nanosilica Following Topical Application." Biomaterials; 2011;32:2713-2724.
Nostro et al.; "Effects of Oregano, Carvacrol and Thymol on *Staphylococcus aureus* and *Staphylococcus epidermidis* Biofilms." J. Med. Microbiol.;2007;56:519-523.

Pereira et al.; "Action of Kanamycin Against Single and Dual Species Biofilms of *Escherichia coli* and *Staphylococcus aureus*." J. Microbiol. Res.;2012;2:84-88.
Pickering,; "Emulsions. J. Chem. Soc. Trans."; 1907;91:2001.
Pieranski,;"Two-Dimensional Interfacial Colloidal Crystals. Phys. Rev. Lett."; 1980;45:569-572.
Radovic-Moreno et al.;"Surface Charge-Switching Polymeric Nanoparticles for Bacterial Cell Wall-Targeted Delivery of Antibiotics." ACS Nano; 2012;6:4279-4287.
Ramanathan et al.; Cationic Amino Acids Specific Biomimetic Silicification in Ionic Liquid: A Quest to Understand the Formation of 3-D Structures in Diatoms.; PLoS One; 2011:6.
Ramsden,; "Separation of Solids in the Surface-Layers of Solutions and Suspensions" (Observations on Surface-Membranes, Bubbles, Emulsions, and Mechanical Coagulation).;Preliminary Account. Proc. R. Soc. London; 1903;72:156-164.
Rancan et al.; "Skin Penetration and Cellular Uptake of Amorphous Silica Nanoparticles with Variable Size, Surface Functionalization, and Colloidal Stability." ACS Nano; 2012;6:6829-6842.
Ricci et al.; Relationship between the Structural Organization and the Physical Properties of PECVD Nitrogenated Carbons.; J. Mater. Res.;1993;8:480-488.
Rosen et al.; "Surface Functionalization of Silica Nanoparticles with Cysteine: A Low-Fouling Zwitterionic Surface." Langmuir; 2011;27:10507-10513.
Roy et al.; "Mixed-Species Biofilm Compromises Wound Healing by Disrupting Epidermal Barrier Function." J. Pathol.; 2014;233:331-343.
Santra et al.; "Fluorescence Lifetime Measurements to Determine the Core-shell Nanostructure of FITC-Doped Silica Nanoparticles: An Optical Approach to Evaluate Nanoparticle Photostability." J. Lumin.;2006;117:75-82.
Shalel et al,; "The Mechanism of Hemolysis by Surfactants: Effect of Solution Dispersion." J. Colloid Interface Sci.;2002;252:66-76.
Stewart et al."Antibiotic Resistance of Bacteria in Biofilms." Lancet; 2001;358;135:138.
Stober et al.; "Controlled Growth of Monodisperse Silica Spheres in the Micron Size Range." Journal of Colloid and Interface Science,;1968:26:62-69.
Sun et al.; "Advances in Skin Grafting and Treatment of Cutaneous Wounds." Science; 2014;346:941-945.
Szomolay et al. "Adaptive Responses to Antimicrobial Agents in Biofilms." Environ. Microbiol.;2005;7:1186-1191.
Takasao et al.; "Cinnamon Extract Promotes Type I Collagen Biosynthesis via Activation of IGF-I Signaling in Human Dermal Fibroblasts." J. Agric. Food Chem.;2012;60:1193-1200.
Tan et al.; X-Ray Photoelectron Spectroscopy Studies of the Chemical Structure of Polyaniline.; Phys. Rev. B;1989;39:8070-8073.
Duncan, B. et al., "Pickering Emulsions for the Delivery of Antimicrobial Hydrophobics", University of Massachusetts, Amherst; Chemistry Department ResearchFest, Aug. 2013; 1 page.
Watt,; "Mammalian Skin Cell Biology: At the Interface between Laboratory and Clinic."; Science;2014;346:937-940.
Wilhelm et al. "Surfactant-Induced Skin Irritation and Skin Repair." J. Am. Acad. Dermatol.;1994;30:944-949.
Williams et al.; "Preparation of Double Emulsions Using Hybrid Polymer/Silica Particles: New Pickering Emulsifiers with Adjustable Surface Wettability." ACS Appl. Mater. Interfaces; 2014;6:20919-20927.
Zhu et al.; "Nanomedicine in the Management of Microbial Infection—Overview and Perspectives." Nano Today; 2014;9:478-498.
Williams et al.; "Preparation of Double Emulsions Using Hybrid Polymer/Silica Particles: New Pickering Emulsifiers with Adjustable Surface Wettability." ACS Appl. Mater. Interfaces; 2014;6; Supporting Information; 15 pages.

* cited by examiner

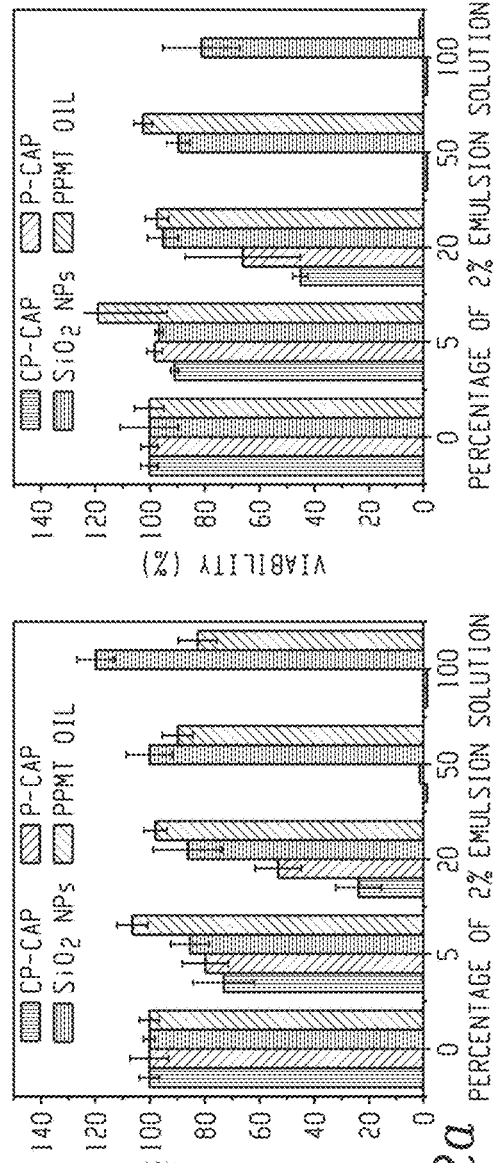
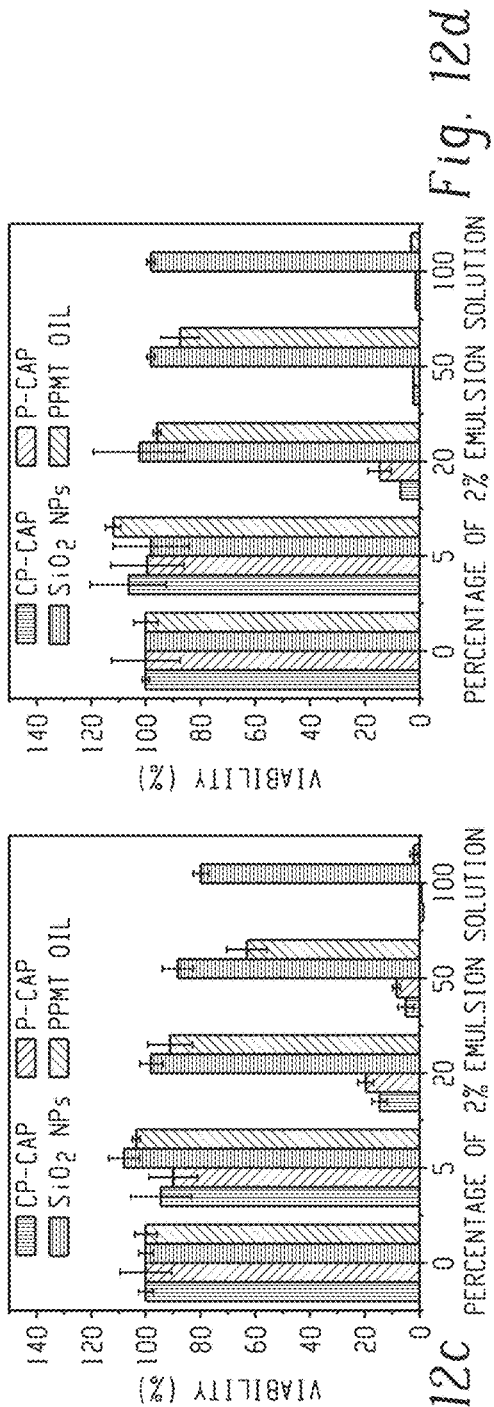
Fig. 12a  Fig. 12b
Fig. 12c  Fig. 12d

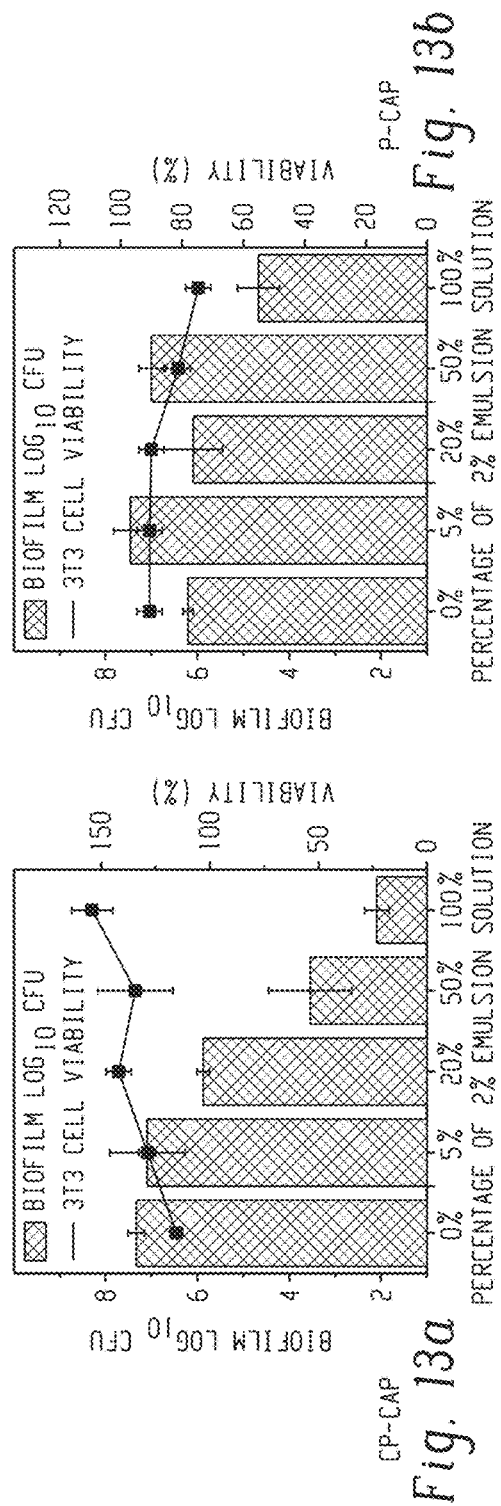
*Fig. 13a* CP-CAP
*Fig. 13b* P-CAP
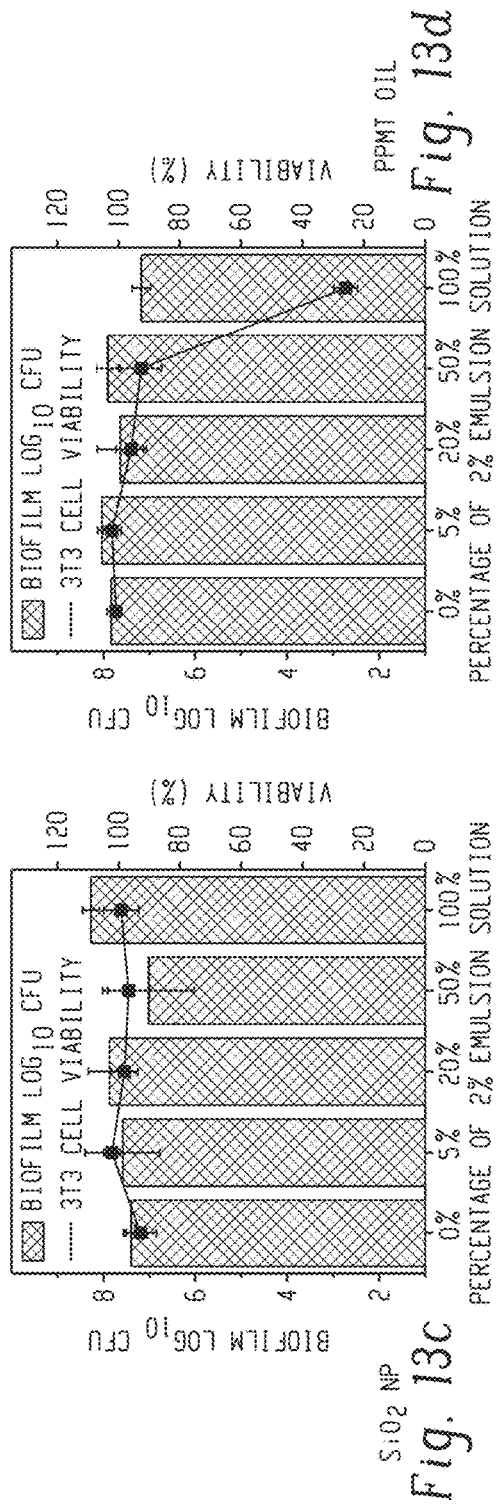
*Fig. 13c* SiO2 NP
*Fig. 13d* PPMT OIL

NANOPARTICLE-STABILIZED MICROCAPSULES, DISPERSIONS COMPRISING NANOPARTICLE-STABILIZED MICROCAPSULES, AND METHOD FOR THE TREATMENT OF BACTERIAL BIOFILMS

STATEMENT REGARDING FEDERALLY SPONSORED RESEARCH & DEVELOPMENT

This invention was made with government support under Grant Number EB014277 awarded by the National Institute of Health (NIH) and under Grant Number CMMI-1025020 awarded by the National Science Foundation (NSF) Center for Hierarchical Manufacturing. The government has certain rights in the invention.

BACKGROUND OF THE INVENTION

Bacterial biofilms are highly resilient microbial assemblies that are difficult to eradicate. See, e.g., Costerton, J. W.; Stewart, P. S.; Greenburg, E. P. Bacterial Biofilms: A Common Cause of Persistent Infections. *Science* 1999, 284, 1318-1322. These robust biofilms frequently occur on synthetic implants and indwelling medical devices including urinary catheters, arthro-prostheses, and dental implants. See, e.g., Lindsay, D.; von Holy, A. Bacterial Biofilms within the Clinical Setting: What Healthcare Professionals Should Know. *J. Hosp. Infect.* 2006, 64, 313-325; Costerton, J. W.; Montanaro, L.; Arciola, C. R. Biofilm in Implant Infections: Its Production and Regulation. *Int. J. Artif. Organs* 2005, 28, 1062-1068; Busscher, H. J.; Rinastiti, M.; Siswomihardjo, W.; van der Mei, H. C. Biofilm Formation on Dental Restorative and Implant Materials. *J. Dent. Res.* 2010, 89, 657-665. Biofilm proliferation can also occur on dead or living tissues, leading to endocarditis, otitis media, and chronic wounds. See, e.g., Costerton, W.; Veeh, R.; Shirtliff, M.; Pasmore, M.; Post, C.; Ehrlich, G. The Application of Biofilm Science to the Study and Control of Chronic Bacterial Infections. *J. Clin. Invest.* 2003, 112, 1466-1477; Ehrlich, G.; Veeh, R.; Wang, X.; Costerton, J. W.; Hayes, J. D.; Hu, F. Z.; Daigle, B. J.; Ehrlich, M. D.; Post, J. C. Mucosal Biofilm Formation on Middle-Ear Mucosa in the Chinchilla Model of Otitis Media. *JAMA* 2002, 287, 1710; James, G. A; Swogger, E.; Wolcott, R.; Pulcini, E. deLancey; Secor, P.; Sestrich, J.; Costerton, J. W.; Stewart, P. S. Biofilms in Chronic Wounds. *Wound Repair Regen.* 2007, 16, 37-44. The persistent infections and their concomitant diseases are challenging to treat, as biofilms develop a high resistance to host immune responses and the extracellular polymeric substances limit antibiotic penetration into biofilms. See, e.g., Stewart, P. S.; Costerton, J. W. Antibiotic Resistance of Bacteria in Biofilms. *Lancet* 2001, 358, 135-138; Szomolay, B.; Klapper, I.; Dockery, J.; Stewart, P. S. Adaptive Responses to Antimicrobial Agents in Biofilms. *Environ. Microbiol.* 2005, 7, 1186-1191. Current techniques to remove biofilms on man-made surfaces include disinfecting the surface with bleach or other caustic agents. See, e.g., Marion-Ferey, K.; Pasmore, M.; Stoodley, P.; Wilson, S.; Husson, G. P.; Costerton, J. W. Biofilm Removal from Silicone Tubing: An Assessment of the Efficacy of Dialysis Machine Decontamination Procedures Using an in Vitro Model. *J. Hosp. Infect.* 2003, 53, 64-71. Biofilms in biomedical contexts are very challenging, with therapies based on excising infected tissues combined with long-term antibiotic therapy, incurring high health care costs and low patient compliance due to the invasive treatment. See, e.g., Lynch, A. S.; Robertson, G. T. Bacterial and Fungal Biofilm Infections. *Annu. Rev. Med.* 2008, 59, 415-428. This issue is exacerbated by the exponential rise in antibiotic resistant bacteria. See, e.g., Levy, S. B.; Marshall, B. Antibacterial Resistance Worldwide: Causes, Challenges and Responses. *Nat. Med.* 2004, 10, S122-S129.

Phytochemicals have emerged as a promising alternative to traditional antimicrobials to treat antibiotic resistant bacteria. See, e.g., Kalemba, D.; Kunicka, A. Antibacterial and Antifungal Properties of Essential Oils. *Curr. Med. Chem.* 2003, 10, 813-829; Hemaiswarya, S.; Kruthiventi, A. K.; Doble, M. Synergism between Natural Products and Antibiotics against Infectious Diseases. *Phytomedicine* 2008, 15, 639-652. These essential oils and natural compounds are of particular interest as "green" antimicrobial agents due to their low-cost, biocompatibility, and potential anti-biofilm properties. See, e.g., Burt, S. Essential Oils: Their Antibacterial Properties and Potential Applications in Foods—a Review. *Int. J. Food Microbiol.* 2004, 94, 223-253; Kavanaugh, N. L.; Ribbeck, K. Selected Antimicrobial Essential Oils Eradicate *Pseudomonas* Spp. and *Staphylococcus Aureus* Biofilms. *Appl. Environ. Microbiol.* 2012, 78, 4057-4061; Nostro, A.; Sudano Roccaro, A.; Bisignano, G.; Marino, A.; Cannatelli, M. A; Pizzimenti, F. C.; Cioni, P. L.; Procopio, F.; Blanco, A. R. Effects of Oregano, Carvacrol and Thymol on *Staphylococcus Aureus* and *Staphylococcus Epidermidis* Biofilms. *J. Med. Microbiol.* 2007, 56, 519-523. The generally poor aqueous solubility and stability of these oils has substantially limited their widespread application. See, e.g., Chen, H.; Davidson, P. M.; Zhong, Q. Impacts of Sample Preparation Methods on Solubility and Antilisterial Characteristics of Essential Oil Components in Milk. *Appl. Environ. Microbiol.* 2014, 80, 907-916. Engineering nanomaterials provides a potential platform to prevent payload degradation and to tune molecular interactions with bacteria. See, e.g., Carpenter, A. W.; Worley, B. V; Slomberg, D. L.; Schoenfisch, M. H. Dual Action Antimicrobials: Nitric Oxide Release from Quaternary Ammonium-Functionalized Silica Nanoparticles. *Biomacromolecules* 2012, 13, 3334-3342; Zhu, X.; Radovic-Moreno, A. F.; Wu, J.; Langer, R.; Shi, J. Nanomedicine in the Management of Microbial Infection—Overview and Perspectives. *Nano Today* 2014, 9, 478-498; Radovic-Moreno, A. F.; Lu, T. K.; Puscasu, V. a; Yoon, C. J.; Langer, R.; Farokhzad, O. C. Surface Charge-Switching Polymeric Nanoparticles for Bacterial Cell Wall-Targeted Delivery of Antibiotics. *ACS Nano* 2012, 6, 4279-4287; Goswami, S.; Thiyagarajan, D.; Das, G.; Ramesh, A. Biocompatible Nanocarrier Fortified with a Dipyridinium-Based Amphiphile for Eradication of Biofilm. *ACS Appl. Mater. Interfaces* 2014, 6, 16384-16394. Previous reports have shown that encapsulating essential oils into surfactant-stabilized colloidal delivery vehicles improves their aqueous stability and increases the antimicrobial activity of small molecule payloads. See, e.g., Chang, Y.; McLandsborough, L.; McClements, D. J. Physicochemical Properties and Antimicrobial Efficacy of Carvacrol Nanoemulsions Formed by Spontaneous Emulsification. *J. Agric. Food Chem.* 2013, 61, 8906-8913; Liang, R.; Xu, S.; Shoemaker, C. F.; Li, Y.; Zhong, F.; Huang, Q. Physical and Antimicrobial Properties of Peppermint Oil Nanoemulsions. *J. Agric. Food Chem.* 2012, 60, 7548-7555; Gomes, C.; Moreira, R. G.; Castell-Perez, E. Poly (DL-Lactide-Co-Glycolide) (PLGA) Nanoparticles with Entrapped Trans-Cinnamaldehyde and Eugenol for Antimicrobial Delivery Applications. *J. Food Sci.* 2011, 76, N16-N24. However, these carriers often induce adverse hemolytic or irritating effects restricting their compatibility with biological tissues. See, e.g., Shalel, S.; Streichman, S.; Marmur, A. The Mechanism of Hemolysis by Surfactants: Effect of Solution Dispersion. *J. Colloid Interface Sci.* 2002, 252, 66-76; Wilhelm, K.-P.; Freitag, G.; Wolff, H. H. Surfactant-Induced Skin Irritation and Skin Repair. *J. Am. Acad. Dermatol.* 1994, 30, 944-949. Pickering emulsions provide an analogous route to encapsulate hydrophobic molecules within a self-assembled colloidal shell that is highly resistant to coalescence. See, e.g., Ramsden, W. Separation of Solids in the Surface-Layers of Solutions and "Suspensions" (Observations on Surface-Membranes, Bubbles, Emulsions, and Mechanical Coagulation).—Preliminary Account. *Proc. R. Soc. London* 1903, 72, 156-164; Pickering, S. U. Emulsions. *J. Chem. Soc. Trans.* 1907, 91, 2001. The multivalent nanoparticles embedded at the oil/water interface can also be post-functionalized to create structurally diverse carriers not achievable when using surfactant stabilized emulsions. See, e.g., Binks, B. P. Particles as Surfactants—Similarities and Differences. *Curr. Opin. Colloid Interface Sci.* 2002, 7, 21-41; Ghouchi Eskandar, N.; Simovic, S.; Prestidge, C. A. Nanoparticle Coated Submicron Emulsions: Sustained in-Vitro Release and Improved Dermal Delivery of All-Trans-Retinol. *Pharm. Res.* 2009, 26, 1764-1775.

BRIEF SUMMARY OF EMBODIMENTS OF THE INVENTION

One embodiment is a stabilized microcapsule comprising a liquid hydrophobic core comprising an essential oil and an aromatic monoaldehyde; and a shell encapsulating the core, the shell comprising a plurality of amino-functionalized inorganic nanoparticles.

Another embodiment is a stabilized microcapsule comprising a liquid hydrophobic core comprising an essential oil; and a shell encapsulating the core, the shell comprising a plurality of amino-functionalized inorganic nanoparticles, wherein the amino-functionalized inorganic nanoparticles further comprise a reaction product covalently bound to a surface of the nanoparticle, wherein the reaction product is formed from reaction of an amino-functionalized inorganic nanoparticle and an aromatic monoaldehyde.

Another embodiment is a dispersion comprising a plurality of stabilized microcapsules.

Another embodiment is a method of treating a bacterial biofilm, the method comprising contacting the dispersion with a bacterial biofilm.

These and other embodiments are described in detail below.

BRIEF DESCRIPTION OF THE DRAWINGS

The following Figures are exemplary embodiments.

FIG. 12a shows the viability of 1 day-old *P. aeruginosa* (CD-1006) biofilms after 3 hours treatment with CP-Cap, P-Cap, $SiO_2$ NP, and peppermint oil at different emulsion concentrations (v/v % of 2% emulsion). The data are average of triplicates and the error bars indicate the standard deviations.

FIG. 12b shows the viability of 1 day-old *E. coli* DH5α biofilms after 3 hours treatment with CP-Cap, P-Cap, $SiO_2$ NP, and peppermint oil at different emulsion concentrations (v/v % of 2% emulsion). The data are average of triplicates and the error bars indicate the standard deviations.

FIG. 12c shows the viability of 1 day-old *S. aureus* (CD-489) biofilms after 3 hours treatment with CP-Cap, P-Cap, SiO$_2$ NP, and peppermint oil at different emulsion concentrations (v/v % of 2% emulsion). The data are average of triplicates and the error bars indicate the standard deviations.

FIG. 12d shows the viability of 1 day-old *E. cloacae* complex (CD-1412) biofilms after 3 hours treatment with CP-Cap, P-Cap, SiO$_2$ NP, and peppermint oil at different emulsion concentrations (v/v % of 2% emulsion). The data are average of triplicates and the error bars indicate the standard deviations.

FIG. 13a shows the viability of 3T3 fibroblast cells and *E. coli* biofilms in the co-culture model after 3 hours treatment with CP-Cap at different emulsion concentrations (v/v % of 2% emulsion). Scatters and lines represent 3T3 fibroblast cell viability. Bars represent log$_{10}$ of colony forming units in biofilms. The data are average of triplicates and the error bars indicate the standard deviations.

FIG. 13b shows the viability of 3T3 fibroblast cells and *E. coli* biofilms in the co-culture model after 3 hours treatment with P-Cap at different emulsion concentrations (v/v % of 2% emulsion). Scatters and lines represent 3T3 fibroblast cell viability. Bars represent log$_{10}$ of colony forming units in biofilms. The data are average of triplicates and the error bars indicate the standard deviations.

FIG. 13c shows the viability of 3T3 fibroblast cells and *E. coli* biofilms in the co-culture model after 3 hours treatment with SiO$_2$ NP at different emulsion concentrations (v/v % of 2% emulsion). Scatters and lines represent 3T3 fibroblast cell viability. Bars represent log$_{10}$ of colony forming units in biofilms. The data are average of triplicates and the error bars indicate the standard deviations.

FIG. 13d shows the viability of 3T3 fibroblast cells and *E. coli* biofilms in the co-culture model after 3 hours treatment with peppermint oil at different emulsion concentrations (v/v % of 2% emulsion). Scatters and lines represent 3T3 fibroblast cell viability. Bars represent log$_{10}$ of colony forming units in biofilms. The data are average of triplicates and the error bars indicate the standard deviations.

DETAILED DESCRIPTION OF THE INVENTION

Figure 1:
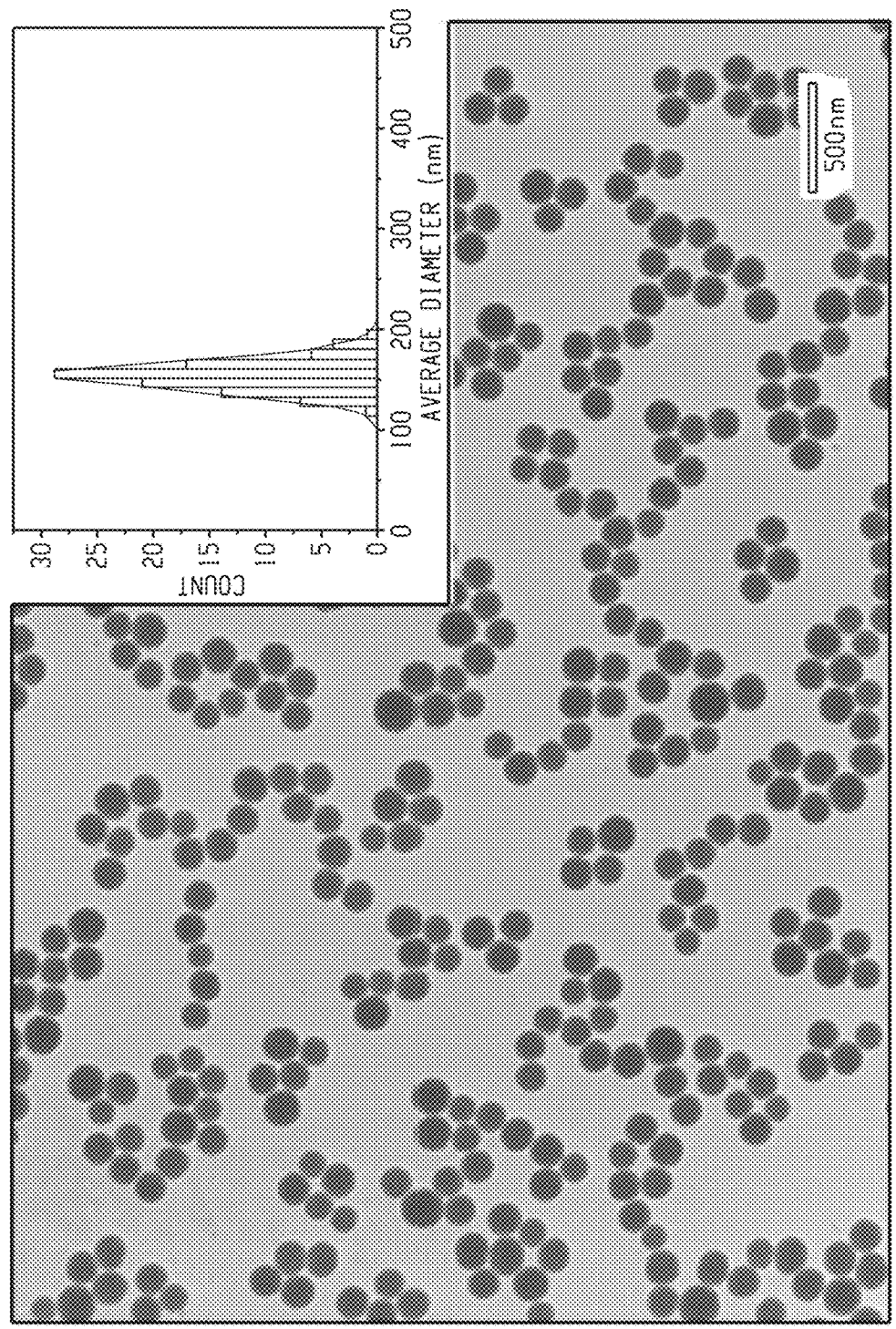
FIG. 1 shows a transmission electron micrograph (TEM) of silica nanoparticles. The nanoparticles had an average diameter of 152±15 nanometers (nm). Inset is a histogram of the measured nanoparticle diameters. Scale bar is 500 nm.

Disclosed herein is the fabrication of a multifunctional essential oil-based Pickering emulsion. The emulsions can be particularly useful for the treatment of bacterial biofilms. The self-assembly strategy relies on hydrophobic phytochemicals playing both antimicrobial and structural roles for the drug delivery vehicle. Droplets comprising an essential oil, such as peppermint oil, provide the main hydrophobic core template for nanoparticle assembly into microcapsules. Dissolved cinnamaldehyde plays a dual role within the oil core by covalently reacting with the nanoparticles at the interface to modify the shell of the capsules from within and acting as a potent antimicrobial agent once delivered into the biofilm. These microcapsules effectively eradicate both laboratory and pathogenic biofilms. The inclusion of cinnamaldehyde also enhanced fibroblast proliferation promoting therapeutic behavior of the capsules as demonstrated in an in vitro co-culture model. See, e.g., Takasao, N.; Tsuji-Naito, K.; Ishikura, S.; Tamura, A.; Akagawa, M. Cinnamon Extract Promotes Type I Collagen Biosynthesis via Activation of IGF-I Signaling in Human Dermal Fibroblasts. *J. Agric. Food Chem.* 2012, 60, 1193-1200. This work presents a versatile colloidal strategy for multicomponent essential oil formulations with potential use as a general topical antimicrobial and disinfectant Accordingly, one aspect of the present disclosure is a stabilized microcapsule. The stabilized microcapsule has a core-shell morphology. In some embodiments, the stabilized microcapsule comprises a liquid hydrophobic core comprising an essential oil and an aromatic monoaldehyde. In some embodiments, the stabilized microcapsule comprises a liquid hydrophobic core comprising an essential oil (e.g., no free, unreacted aromatic monoaldehyde is present). The liquid hydrophobic core is generally a liquid at 25° C. The essential oil can be a naturally occurring compound (e.g., derived from a plant). Essential oils, as used herein, are volatile aromatic oils which can be synthetic or derived from plants (e.g., flowers, buds, seeds, leaves, twigs, bark, herbs, wood, fruits, roots, and the like) by a physical method (e.g., distillation, expression, fermentation, or extraction). Essential oils usually carry the odor or flavor of the plant from which they are obtained. The essential oil is preferably an oil having antimicrobial properties. In some embodiments, the essential oil can be selected from, for example, peppermint oil, oregano oil, thymol, menthol, methyl salicylate (wintergreen oil), eucalyptol, carvacrol, camphor, anethole, carvone, eugenol, isoeugenol, limonene, osimen, n-decyl alcohol, citronel, a-salpineol, methyl acetate, citronellyl acetate, methyl eugenol, cineol, linalool, ethyl linalaol, safrola vanillin, spearmint oil, lemon oil, orange oil, sage oil, rosemary oil, cinnamon oil, pimento oil, laurel oil, cedar leaf oil, clove oil, cilantro oil, coriander oil, or a combination thereof. In some embodiments, the essential oil is selected from peppermint oil, cilantro oil, coriander oil, cinnamon oil, oregano oil, rosemary oil, sage oil, clove oil, thyme oil, or a combination thereof. In some embodiments, the essential oil is peppermint oil. In some embodiments, the essential oil is present in an amount of 90 to 99 or 95 to 99 weight percent, based on the total weight of the core. In some embodiments, the essential oil is present in an amount of 90 to 99.9, or 90 to 99, or 95 to 99 volume percent, based on the total volume of the core.

In addition to the essential oil, the liquid hydrophobic core of the microcapsule can include an aromatic monoaldehyde. The aromatic monoaldehyde is miscible with the essential oil. In some embodiments, the aromatic monoaldehyde is cinnamaldehyde. Cinnamaldehyde (also known as cinnamic aldehyde or 3-phenyl-2-propenal) is a main component of cassia oil and cinnamon bark oil. Cinnamaldehyde is also a major antimicrobial compound in cinnamon. In some embodiments, the aromatic monoaldehyde is present in an amount of 0.01 to 10, or 0.1 to 10, or 1 to 10, or 1 to 5 volume percent, based on the total volume of the essential oil and the aromatic monoaldehyde (i.e., the total volume of the liquid hydrophobic core). In some embodiments, the aromatic monoaldehyde is present in an amount of 0.01 to 10, or 0.1 to 10, or 1 to 10, or 1 to 5 weight percent, based on the total weight of the core.

In some embodiments, the total weight of the core (e.g., the weight of the essential oil and the aromatic monoaldehyde) constitutes 90 to 99, or 92 to 98, or 94 to 96 weight percent of the total weight of the microcapsule.

In addition to the liquid hydrophobic core, the microcapsule of the present disclosure comprises a shell encapsulating the core. The shell comprises a plurality of amino-functionalized inorganic nanoparticles. In some embodiments, the shell comprises a monolayer of amino-functionalized inorganic nanoparticles. The inorganic nanoparticles can be metal nanoparticles, metal alloy nanoparticles, metal oxide nanoparticles, or a combination thereof. The nanoparticles generally have one or more dimensions of less than 1000 nanometers, for example less than 500 nanometers, for example, less than 250 nanometers. In some embodiments, the nanoparticles are spherical nanoparticles. In some embodiments, the nanoparticles are silica nanoparticles, silicon nanoparticles, gold nanoparticles, titanium oxide nanoparticles, and the like, or a combination thereof. In some embodiments, the nanoparticles comprise silica, titanium dioxide, or a combination thereof. In some embodiments, the inorganic nanoparticles comprise silica, for example the inorganic nanoparticles can be silica nanoparticles. In some embodiments, the inorganic nanoparticles have an average diameter of 75 to 500 nanometers, or 100 to 250 nanometers, or 100 to 200 nanometers, or 125 to 175 nanometers, or 135 to 170 nanometers, or 140 to 160 nanometers.

The inorganic nanoparticles are amino-functionalized nanoparticles. "Amino-functionalized" means that one or more amino functional groups are present on the surface of the nanoparticle. In some embodiments, the amino functional group is covalently bound to the surface of the nanoparticles. In some embodiments, the amino-functionalized nanoparticles include a linker between the amino group and the surface of the nanoparticle, for example a linker comprising a $C_{1-12}$ alkyl group, a $C_{6-20}$ aryl group, or an alkylene amino group. In some embodiments, the amino group can be directly bound to the surface of the nanoparticle (i.e., no linker is present). In some embodiments, for example when the nanoparticle is a metal nanoparticle, the amino functional group can be covalently bound to a ligand that is associated with the surface of the nanoparticle though ligand-type interactions. The chemical structure of the ligand can be selected by those skilled in the art with regards to the specific ligand-type interaction and strength of those interactions with the nanoparticle. The ligand-type interaction can be any suitable bonding or non-bonding interaction. Ligand type interactions comprise high affinity or low affinity site-specific type interactions, non-bonded electrostatic interactions such as electropositive or electronegative type or van der Waals repulsive and attractive forces, ionic bonds, hydrogen bonds, coordination bonds, or a combination thereof. For example, a gold nanoparticle can interact with a thiol-functionalized ligand including the amino functional group. In some embodiments, the amino group is a primary amino group.

In some embodiments, when the nanoparticles comprise silica, the surface of the silica nanoparticle can be functionalized through reaction of the silica with an aminosilane, for example aminopropyl trimethoxysilane, aminopropyl triethoxysilane, or the like. The silane can react with the silica to provide primary amine groups covalently attached to the nanoparticle surface. An extensive range of silanes exist and can be selected by those skilled in the art to provide the desired amino-functionalized nanoparticle.

In some embodiments, an amino-functionalized nanoparticle of the microcapsule shell can react with the aromatic monoaldehyde present in the core to provide a corresponding reaction product. For example, the portion of the surface of the nanoparticle that is exposed to and in contact with the liquid hydrophobic core can react with one or more aromatic monoaldehydes to provide a nanoparticle wherein at least a portion of the surface of the nanoparticle comprises the reaction product of the amino-functionalized nanoparticle and the aromatic monoaldehyde, thus promoting the formation of Janus-type particles, defined as a particle having two distinct regions (e.g., hemispheres) of functionality. The aromatic monoaldehyde can be linked to the surface of the nanoparticle by formation of the corresponding aromatic imine (—C=N—). Thus, in some embodiments, the shell of the microcapsule can comprise amino-functionalized nanoparticles, inorganic nanoparticles covalently bound to a reaction product formed from reaction of an amino group and an aromatic monoaldehyde, or a combination thereof. In some embodiments, the inorganic nanoparticles can include both an amino functional group and the corresponding imino-linked reaction product bound to the surface of the nanoparticle, preferably wherein substantially all of the imino-linked reaction product is in contact with the core of the microcapsule. Stated another way, the microcapsule can include a shell comprising inorganic nanoparticles, wherein each nanoparticle has two regions of functionality: the first region comprises an amino functional group, and the second region comprises a reaction product formed from reaction of the amino functional group and an aromatic monoaldehyde. In an embodiment, the second region of each nanoparticle is in contact with the core. In some embodiments, substantially all of the aromatic monoaldehyde can be reacted such that the core of the microcapsule contains no free aromatic monoaldehyde.

In some embodiments, the nanoparticles can have a zeta potential of 5 to 25 millivolts (mV), or 10 to 20 mV, or 15 to 18 mV, or 16 to 17 mV. In some embodiments, zeta potential of the nanoparticles can be determined at physiological pH, or a pH of 7 to 8, preferably a pH of 7.4.

In some embodiments, the inorganic nanoparticles are present in an amount of 1 to 10 weight percent, or 2 to 8 weight percent, of 4 to 6 weight percent, based on the total weight of the microcapsule.

In some embodiments, the microcapsule has an average diameter of 1 to 50 micrometers, or 1 to 20 micrometers, or 1 to 10 micrometers, or 2 to 10 micrometers, or 4 to 10 micrometers, or 4 to 9 micrometers.

In an embodiment, the microcapsule comprises a liquid hydrophobic core comprising peppermint oil and an aromatic monoaldehyde that is cinnamaldehyde, and a shell comprising amino-functionalized silica nanoparticles having an average diameter of 140 to 160 nanometers. The microcapsule includes 1 to 5 volume percent cinnamaldehyde based on the total volume of the core. In this embodiment, the microcapsule has an average diameter of 4 to 9 micrometers.

In an embodiment, the microcapsule comprises a liquid hydrophobic core comprising peppermint oil, and a shell comprising silica nanoparticles having a first region of functionality and a second region of functionality. In this embodiment, the first region of functionality comprises a plurality of amino functional groups bound to the surface of the nanoparticle. Further in this embodiment, the second region of functionality comprises a plurality of ligands formed from the reaction of an amino group bound to the surface of the nanoparticle and cinnamaldehyde (i.e., each ligand is a reaction product formed from the reaction of an amino group bound to the surface of the nanoparticle and cinnamaldehyde). The second region of functionality is in contact with the core of the microcapsule. In this embodiment, the microcapsule has an average diameter of 4 to 9 micrometers.

In an embodiment, the microcapsule comprises 90 to 99 weight percent of the liquid hydrophobic core, and 1 to 10 weight percent of the shell encapsulating the core comprising a plurality of amino-functionalized silica nanoparticles, wherein the weight percent of the core and the shell components are based on the total weight of the microcapsule. In this embodiment, the core comprises 90 to 99 weight percent peppermint oil and 1 to 10 weight percent cinnamaldehyde, based on the total weight of the core.

Another aspect of the present disclosure is a dispersion comprising a plurality of stabilized microcapsules. As used herein, "plurality of microcapsules" refers to a dispersion comprising more than 1 microcapsule, for example more than 10 microcapsules. The microcapsules can include microcapsules having the above-described structure and components. In some embodiments, the dispersion can be in the form of a liquid, a gel, or a paste. In some embodiments, the dispersion can be in the form of a gel or a paste (e.g., a toothpaste). In some embodiments, the stabilized microcapsules are dispersed in an aqueous solution, and the dispersion is in the form of a liquid. The aqueous solution can comprise water, deionized water, a buffer (e.g., phosphate buffered saline, phosphate buffer, and the like), and the like, or a combination thereof. In some embodiments, the dispersion comprises 1 to 50 volume percent (vol. %) of the microcapsules, for example 1 to 20 vol. %, for example 5 to 15 vol. %, based on the total volume of the dispersion. Accordingly, in some embodiments, the dispersion comprises 50 to 99 vol. %, or 80 to 99 vol. %, or 85 to 95 vol. % of the aqueous solution, based on the total volume of the dispersion.

Depending on the pH of the aqueous solution, the amino-functionalized inorganic nanoparticles can be converted to ammonium-functionalized inorganic nanoparticles. Thus in some embodiments, the microcapsules of the dispersion can have a shell comprising amino-functionalized inorganic nanoparticles, ammonium-functionalized inorganic nanoparticles, or a combination thereof. The pH of the aqueous solution can generally be selected by a person skilled in the art in order to provide a microcapsule having the desired surface charge.

In some embodiments, the dispersion excludes a surfactant, for example the dispersion includes less than 1 weight percent of a surfactant, or less than 0.1 weight percent of a surfactant, preferably the dispersion is devoid of a surfactant. In some embodiments, a crosslinker is excluded from the microcapsules, where a crosslinker is defined as a compound having two or more functional groups capable of reaction, for example reaction with a functional group present on the surface of a nanoparticle.

In some embodiments, the dispersion comprises a plurality of microcapsules comprising a core comprising an essential oil (e.g., peppermint oil) and an aromatic monoaldehyde (e.g., cinnamaldehyde) and a shell comprising amino-functionalized inorganic nanoparticles (e.g., silica nanoparticles). When the shell comprises silica, the silica can be present in an amount of less than or equal to 3 weight percent, or 0.05 to 3 weight percent, or 0.1 to 1.5 weight percent, or 0.2 to 1.2 weight percent, or 0.3 to 1.2 weight percent, or 0.5 to 1.2 weight percent, of 0.6 to 1.2 weight percent, based on the total weight of the dispersion.

The dispersions can be prepared by any method that is generally known. For example, the dispersion can be prepared by contacting an aqueous solution comprising the amino-functionalized inorganic nanoparticles with a hydrophobic liquid (e.g., comprising the essential oil and the aromatic monoaldehyde) to form a mixture. The hydrophobic liquid is insoluble in the aqueous solution. Subsequent to contacting the aqueous solution and the hydrophobic liquid, the mixture is emulsified, for example using an amalgamator, or any suitable mixing device. Emulsifying the mixture provides microcapsules comprising the hydrophobic liquid dispersed in the aqueous solution, wherein the microcapsules are stabilized by a shell comprising the amino-functionalized inorganic nanoparticles. An example of a method for preparing a dispersion according to the present disclosure is provided in the working examples below.

Another aspect of the present disclosure is a method for treating a bacterial biofilm. The method comprises contacting the above-described dispersion with a bacterial biofilm. A "biofilm" refers to a population of bacteria attached to an inert or living surface. Thus, biofilms can form on a counter, a table, water pipes, implants, catheters, cardiac pacemakers, prosthetic joints, cerebrospinal fluid shunts, endotracheal tubes, and the like. In some embodiments, the biofilm can be present on a living surface, for example skin or in a wound, and on teeth (e.g., dental plaque). Bacteria in a biofilm are enmeshed in an extracellular polymer matrix, generally a polysaccharide matrix, which holds the bacteria together in a mass, and firmly attaches the bacterial mass to the underlying surface. Evidence has shown that biofilms constitute a significant threat to human health. Wounds and skin lesions are especially susceptible to bacterial infection.

In some embodiments, the bacterial biofilm can be a gram-negative bacterial biofilm or a gram-positive bacterial biofilm. In some embodiments, the bacterial biofilm comprises *Escherichia coli* (e.g., *E. coli* DH5α), *Pseudomonas* bacteria (e.g., *Pseudomonas aeruginosa*), *Staphylococcal* bacteria (e.g., *Staphylococcal aureus*), Enterobacteriaceae bacteria (e.g., *E. cloacae* complex), *Streptococcus* bacteria, *Haemophilus influenzae, Leptospira interrogans, Legionella* bacteria, or a combination thereof.

Contacting the dispersion comprising the microcapsules with a biofilm can effectively kill bacterial cells present in the biofilm. Accordingly, the dispersions disclosed herein can be particularly useful as disinfectants or antimicrobial dispersions. The contacting can be under conditions effective to treat the biofilm, for example for a time of 10 minutes to 5 hours, or 1 hour to 3 hours, and at a temperature of 25 to 37° C. As used herein, "treating a biofilm" can refer to killing at least 20%, or at least 40%, or at least 50%, or at least 60%, or at least 80%, or at least 90% of the bacterial cells present in the biofilm. In some embodiments, contacting the dispersion with a biofilm can completely remove the biofilm (i.e., the dispersion is toxic to greater than 90%, or 99% or 99.9% of the bacterial cells of the biofilm upon contacting the dispersion with the biofilm).

In some embodiments, contacting the dispersion with a biofilm can be in the presence of a host cell, for example, mammalian fibroblasts. In some embodiments, the dispersion is non-toxic to the host cells, for example, at least 75%, or at least 80%, or at least 85%, or at least 90%, or at least 95% of the host cells remain viable after contacting the dispersion. In some embodiments, the host cells can proliferate in the presence of the dispersion, for example the number of host cells can increase by at least a factor of 1.1, or at least a factor of 1.25, or at least a factor of 1.5 after contacting the dispersion.

In summary, the development of a multimodal antimicrobial delivery vehicle is reported herein. The nanoparticle stabilized capsules demonstrate highly effective therapeutic behavior, successfully eradicating pathogenic biofilm strains of clinical isolates. Furthermore, the capsules can effectively eliminate a biofilm infection while promoting fibroblast viability in an in vitro co-culture model. Future studies will probe capsule performance in combating in vivo biofilms. These capsules have potential applications as a general surface disinfectant as well as an antiseptic for wound treatment. The reactive self-assembly based strategy provides a promising platform to create effective delivery vehicles to combat bacterial biofilms.

The microcapsules, dispersions, and methods are further illustrated by the following non-limiting examples.

EXAMPLES

Figure 2:
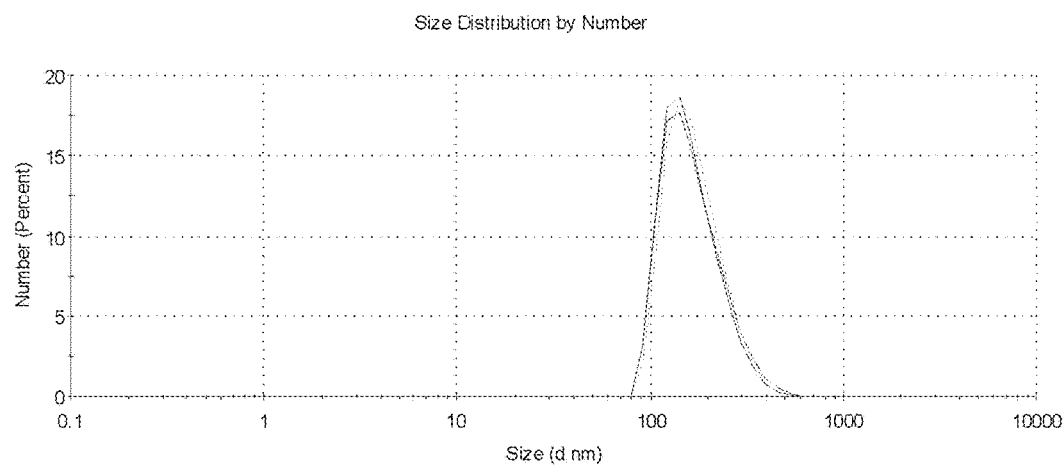
FIG. 2 shows average diameter of the silica nanoparticles in MilliQ $H_2O$ as determined by dynamic light scattering (DLS).
Figure 3:
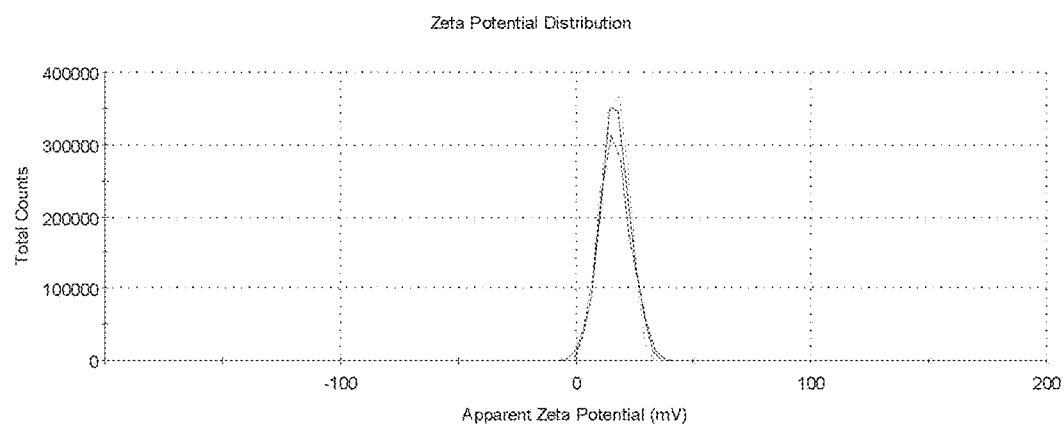
FIG. 3 shows zeta potential of the silica nanoparticles in 5 millimolar (mM) sodium phosphate buffer adjusted to pH 7.4.

Silica nanoparticles ($SiO_2$ NPs) were chosen to stabilize the emulsions as they are biocompatible, surface functionalization can be easily introduced, and their diameters can be readily tuned. See, e.g., Ghouchi Eskandar, N.; Simovic, S.; Prestidge, C. A. Nanoparticle Coated Submicron Emulsions: Sustained in-Vitro Release and Improved Dermal Delivery of All-Trans-Retinol. *Pharm. Res.* 2009, 26, 1764-1775; Stöber, W.; Fink, A.; Bohn, E. Controlled Growth of Monodisperse Silica Spheres in the Micron Size Range. *Journal of Colloid and Interface Science*, 1968, 26, 62-69; Rosen, J. E.; Gu, F. X. Surface Functionalization of Silica Nanoparticles with Cysteine: A Low-Fouling Zwitterionic Surface. *Langmuir* 2011, 27, 10507-10513. Control over the size is especially important as nanomaterials smaller than 70 nm have been shown to readily penetrate the skin causing detrimental side-effects. See, e.g., Rancan, F.; Gao, Q.; Graf, C.; Troppens, S.; Hadam, S.; Hackbarth, S.; Kembuan, C.; Blume-Peytavi, U.; Rühl, E.; Lademann, J.; et al. Skin Penetration and Cellular Uptake of Amorphous Silica Nanoparticles with Variable Size, Surface Functionalization, and Colloidal Stability. *ACS Nano* 2012, 6, 6829-6842; Labouta, H. I.; Schneider, M. Interaction of Inorganic Nanoparticles with the Skin Barrier: Current Status and Critical Review. *Nanomedicine: Nanotechnology, Biology, and Medicine*, 2013, 9, 39-54; Nabeshi, H.; Yoshikawa, T.; Matsuyama, K.; Nakazato, Y.; Matsuo, K.; Arimori, A.; Isobe, M.; Tochigi, S.; Kondoh, S.; Hirai, T.; et al. Systemic Distribution, Nuclear Entry and Cytotoxicity of Amorphous Nanosilica Following Topical Application. *Biomaterials* 2011, 32, 2713-2724. Therefore, we synthesized cationic amino-functionalized $SiO_2$ NPs with an average diameter of ~150 nm, as shown in FIG. 1-3. FIG. 1 shows a transmission electron micrograph (TEM) image of silica nanoparticles having an average diameter of 152±15 nm (scale bar is 500 nm). The inset shows a histogram of the measured nanoparticle diameters. FIG. 2 and FIG. 3 show the results from dynamic light scattering (DLS) and zeta potential measurements, performed using a Malvern Zetasizer Nano ZS. FIG. 2 shows that average diameter of the silica nanoparticles in MilliQ water was 171.5±2.8 nm. FIG. 3 shows that zeta potential of the silica nanoparticles in 5 millimolar (mM) sodium phosphate buffer at pH 7.4 was 16.7±0.1 mV.

Figure 4:
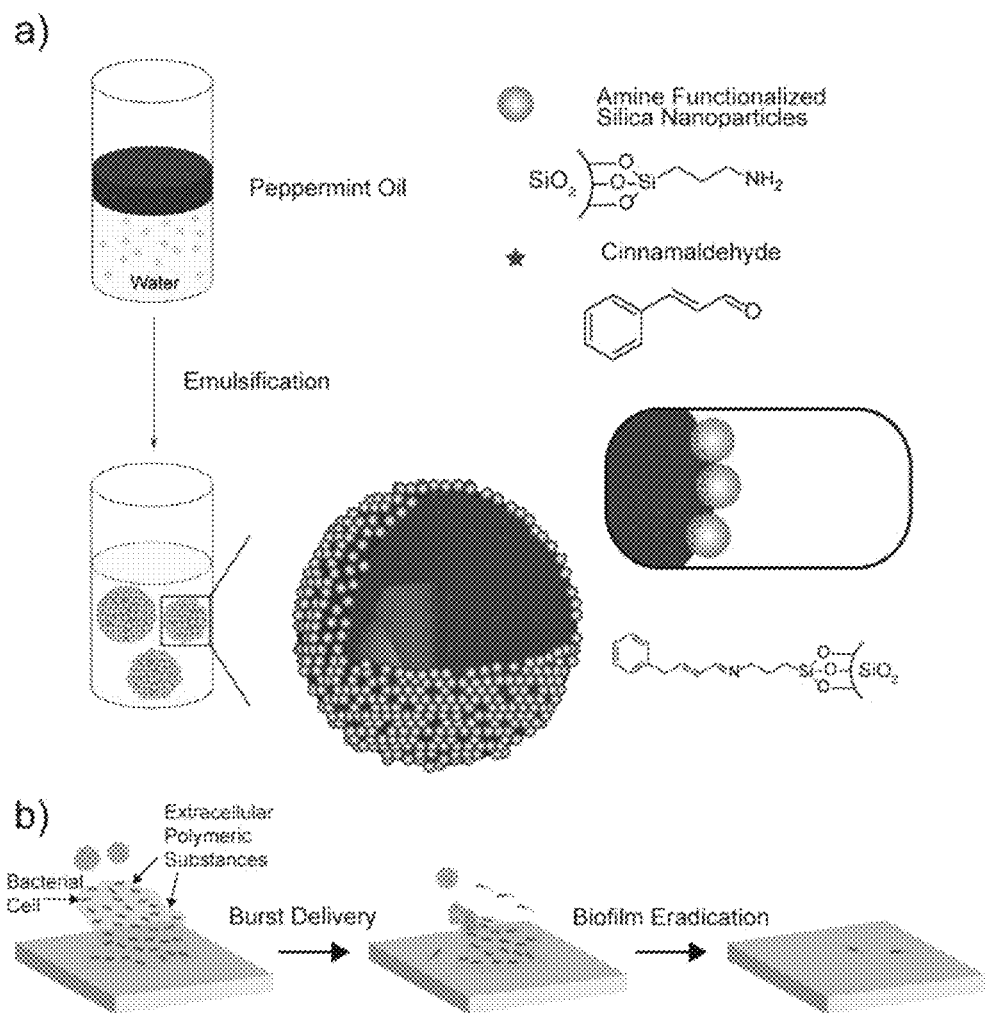
FIG. 4 shows a schematic depiction of the strategy used to generate antimicrobial capsules (a), and subsequent use for treatment of a biofilm (b).
Figure 5A:
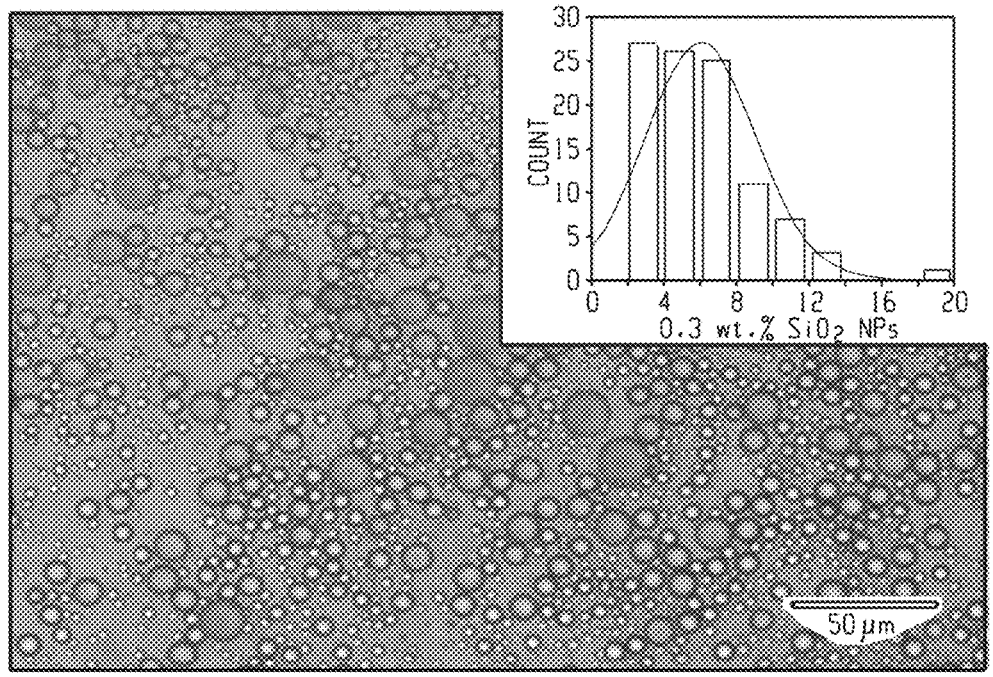
FIG. 5a shows an optical microscopy image of capsules generated using an aqueous phase comprised of 0.3 wt. % silica (average diameter=6.1±3.0 micrometers (μm)). Inset is the histogram of the capsule diameter measurement. Scale bar is 50 μm.
Figure 5B:
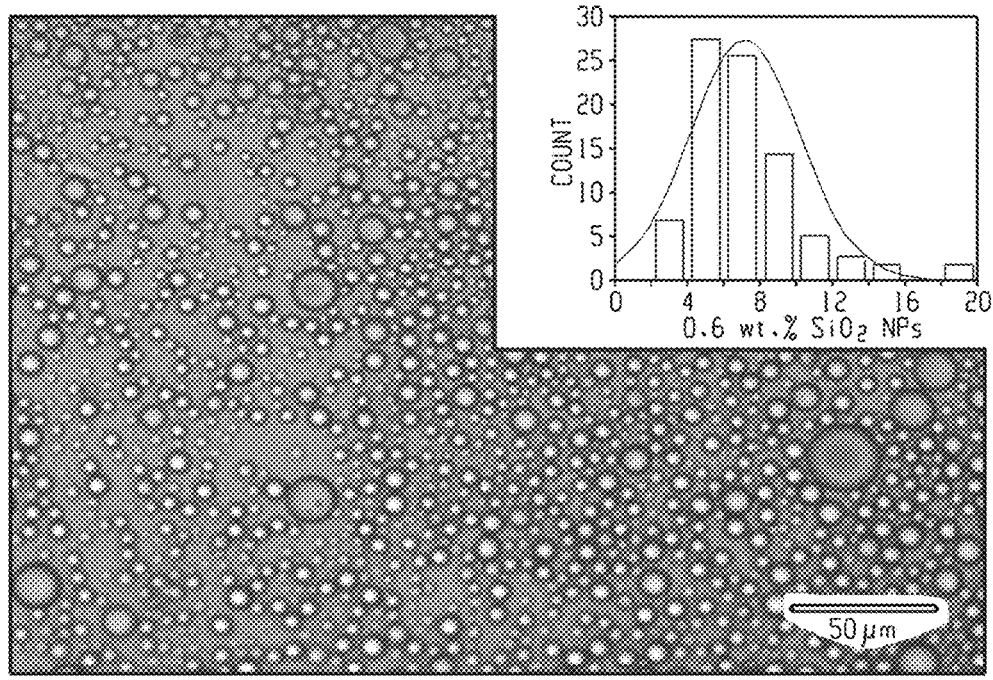
FIG. 5b shows an optical microscopy image of capsules generated using an aqueous phase comprised of 0.6 wt. % silica (average diameter=7.1±3.0 μm). Inset is the histogram of the capsule diameter measurement. Scale bar is 50 μm.
Figure 5C:
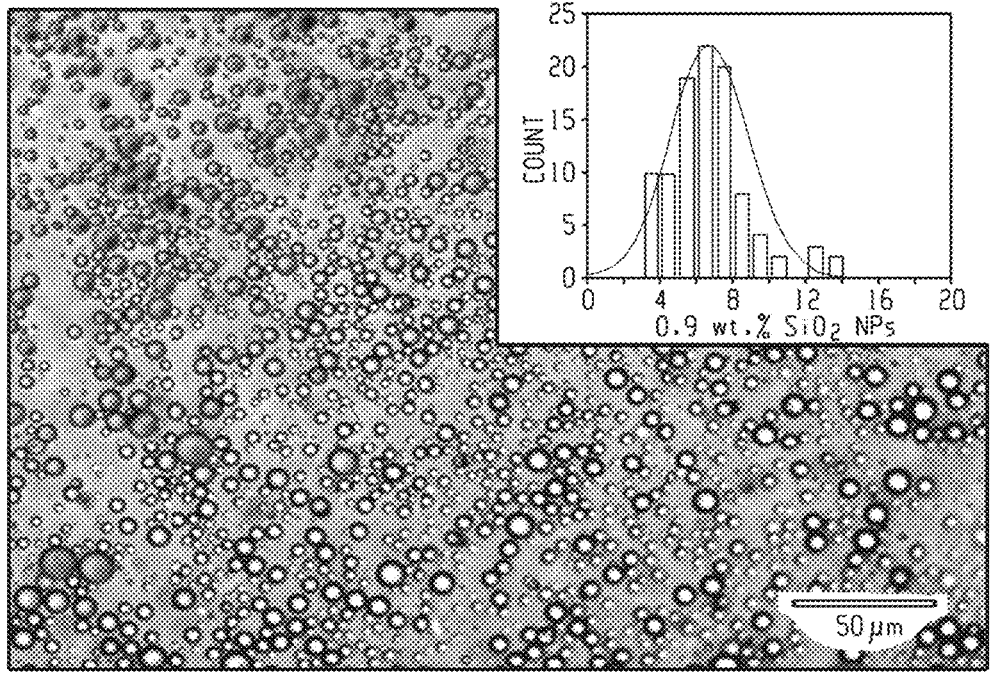
FIG. 5c shows an optical microscopy image of capsules generated using an aqueous phase comprised of 0.9 wt. % silica (average diameter=6.7±2.1 μm). Inset is the histogram of the capsule diameter measurement. Scale bar is 50 μm.
Figure 5D:
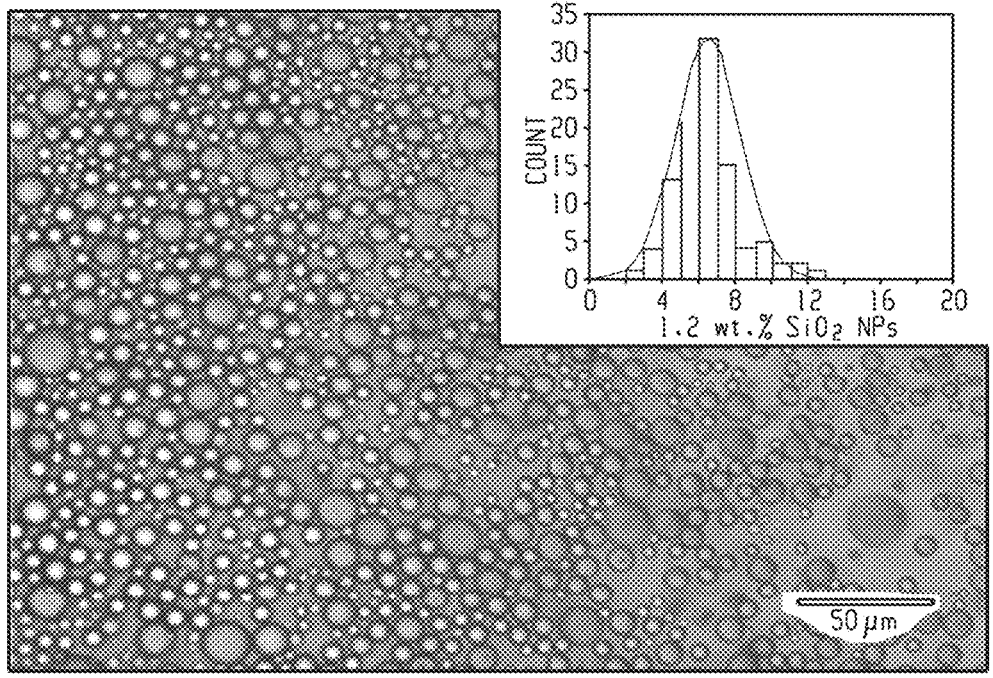
FIG. 5d shows an optical microscopy image of capsules generated using an aqueous phase comprised of 1.2 wt. % silica (average diameter=6.5±1.7 μm). Inset is the histogram of the capsule diameter measurement. Scale bar is 50 μm.
Figure 5E:
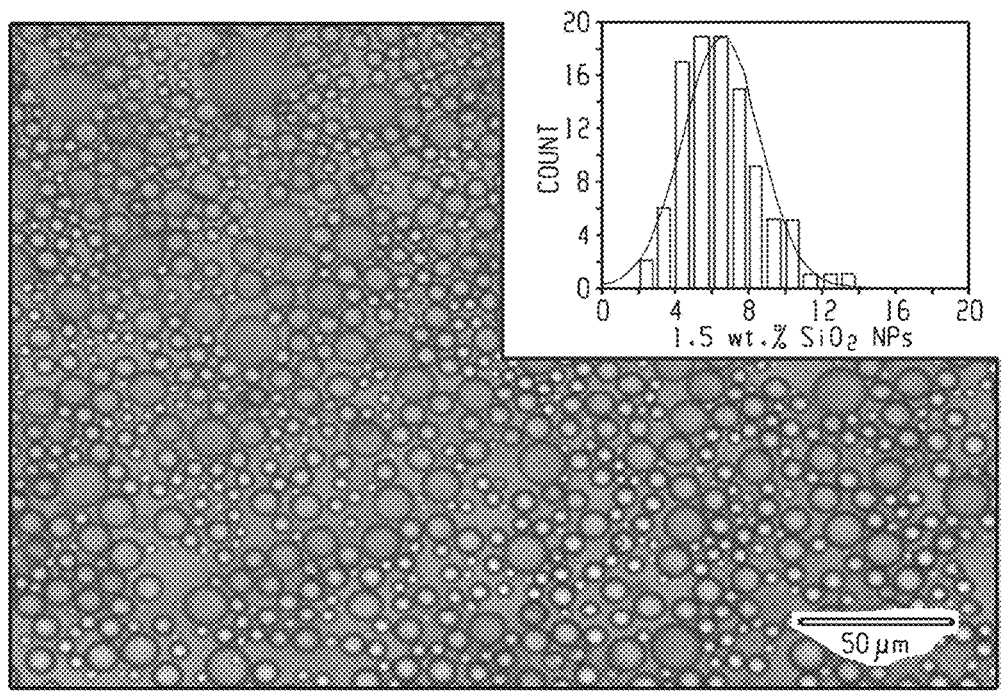
FIG. 5e shows an optical microscopy image of capsules generated using an aqueous phase comprised of 1.5 wt. % silica (average diameter=6.6±2.1 μm). Inset is the histogram of the capsule diameter measurement. Scale bar is 50 μm.
Figure 5F:
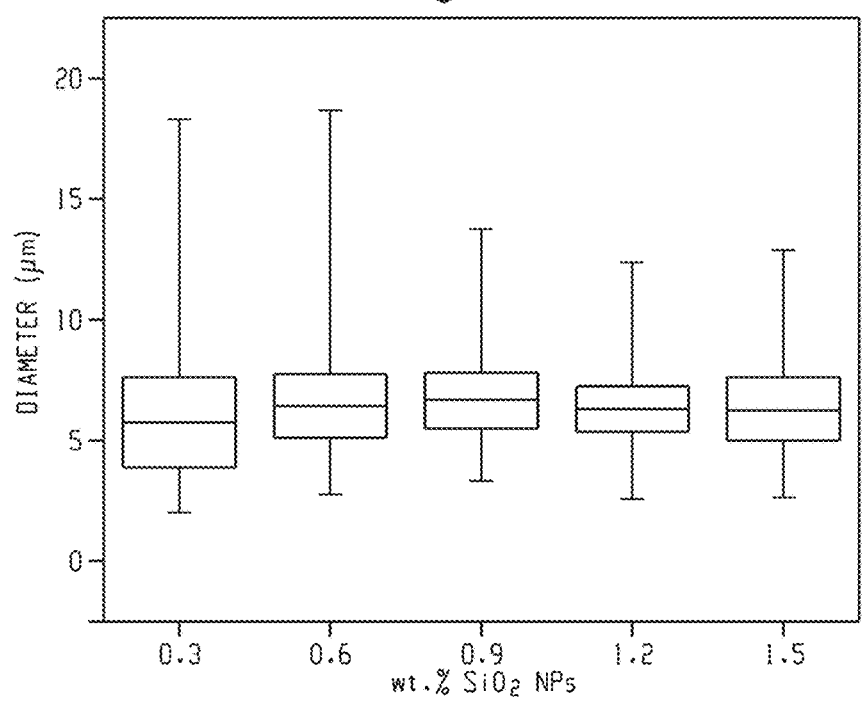
FIG. 5f shows a box plot of the capsules at various silica loadings demonstrating capsule dispersity minimizes with increasing wt. % of silica nanoparticles.

Antimicrobial capsules were generated using a Pickering emulsion template as shown in FIG. 4. As shown in FIG. 4, peppermint oil with dissolved cinnamaldehyde is emulsified into an aqueous suspension of amine functionalized silica nanoparticles. Cinnamaldehyde within the oil reacts with the amines on the nanoparticles at the oil/water interface to create a multimodal delivery vehicle. Capsules can interact with a biofilm through electrostatic complementarity. Capsules release their payload disrupting the biofilm, eliminating the bacteria. Capsules were created by emulsifying either peppermint oil or a mixture of cinnamaldehyde dissolved in peppermint oil into MilliQ $H_2O$ adjusted to a pH of 10 containing the nanoparticles. The nanoparticles self-assemble at the oil/water interface to stabilize the peppermint oil droplets. Surface amines on the nanoparticles then react with the cinnamaldehyde within the oil phase.

Silica loadings in the aqueous phase were varied to determine the amount needed to minimize capsule dispersity. At loadings of 1.2 wt. % $SiO_2$ NPs or greater, capsules were found to have a minimum dispersity and therefore this amount was chosen for all further studies. The effect of $SiO_2$ NP loading is shown in the optical micrographs of FIG. 5. Optical images of the capsules were taken on an Olympus IX51 microscope. Capsules were generated using aqueous phases comprising a) 0.3 wt. % silica (average diameter=6.1±3.0 µm), b) 0.6 wt. % silica (average diameter=7.1±3.0 µm), c) 0.9 wt. % silica (average diameter=6.7±2.1 µm), d) 1.2 wt. % silica (average diameter=6.5±1.7 µm), and e) 1.5 wt. % silica (average diameter=6.6±2.1 µm), respectively. The inset of each micrograph shows the histogram of the capsule diameter measurements. FIG. 5 also shows a box plot of the capsules at various silica loadings demonstrating capsule dispersity minimizes with increasing wt. % of silica nanoparticles.

Figure 6A:
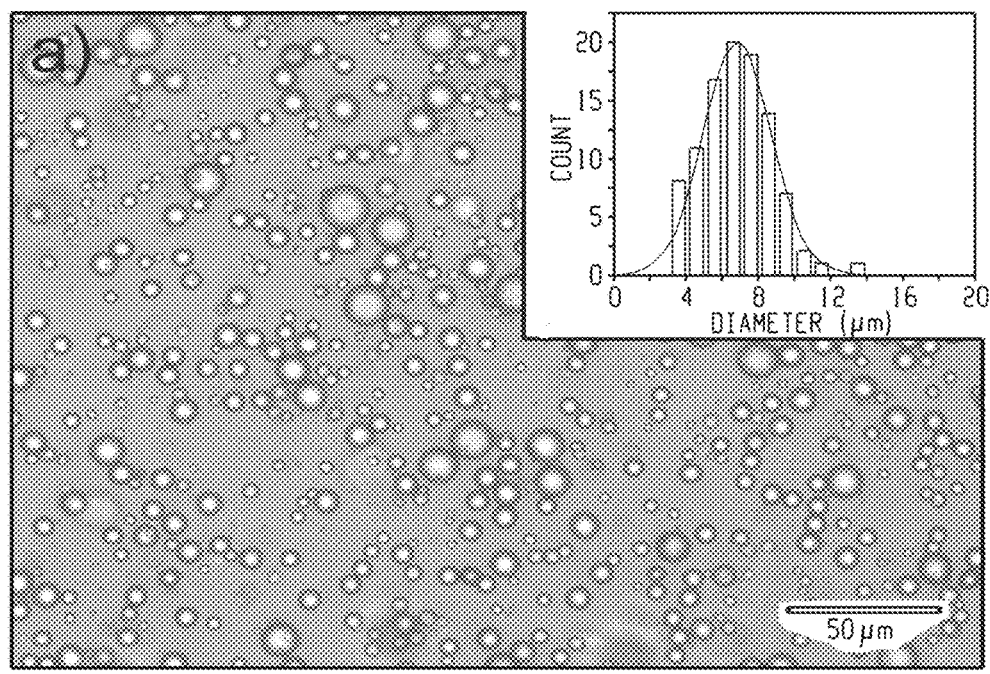
FIG. 6a shows optical an microscopy image of peppermint oil based capsules ("P-Cap").
Figure 6B:
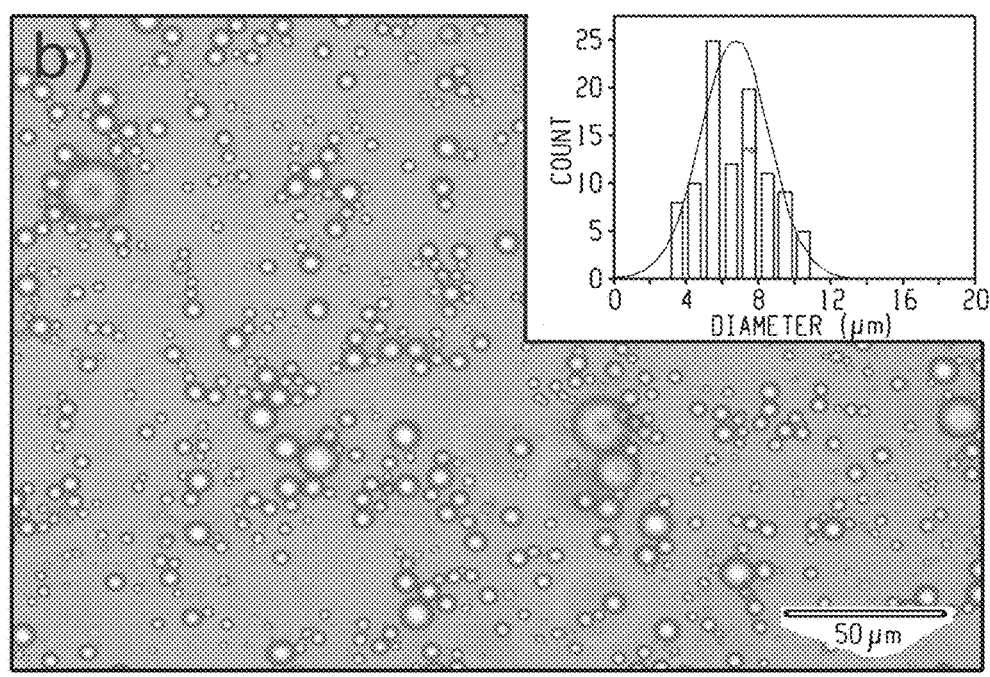
FIG. 6b shows an optical microscopy image of capsules containing 5% v/v of cinnamaldehyde dissolved in peppermint oil ("CP-Cap").

It was also observed that capsules generated with higher than 5% v/v cinnamaldehyde were unstable which corresponds to 52-fold excess of cinnamaldehyde to available amines on the nanoparticle surface. The peppermint oil based capsules ("P-Cap") and capsules containing 5% v/v of cinnamaldehyde dissolved in peppermint oil ("CP-Cap") were found to have average diameters of 6.8±1.9 micrometers (µm) and 6.7±1.9 µm, respectively, as shown in the optical microscopy images of FIG. 6. FIG. 6 shows P-Cap had an average diameter of 6.8±1.9 µm (a) and CP-Cap had an average diameter of 6.7±1.9 µm (b). The insets are histograms of the capsule diameter measurements.

Figure 7B:
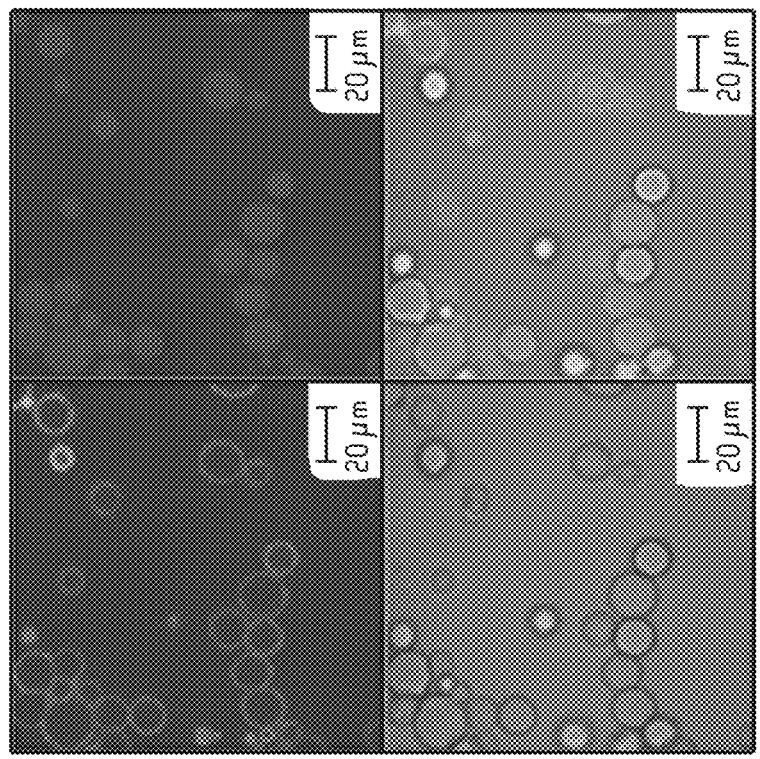
FIG. 7b shows confocal micrographs of CP-Cap. The nanoparticles' cores are labeled with fluorescein and the oil phases are loaded with Nile red. Scale bars are 20 μm.
Figure 7A:
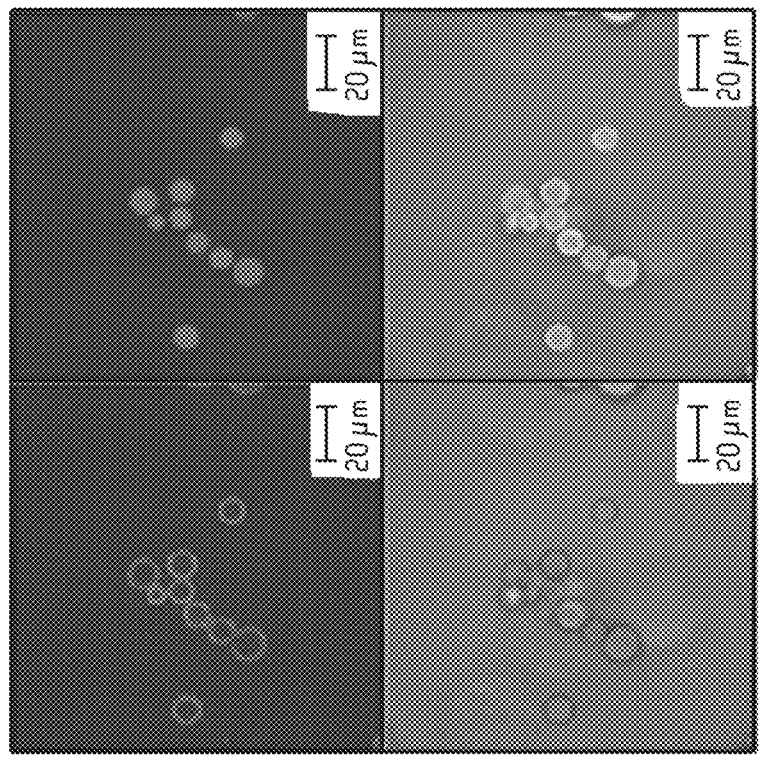
FIG. 7a shows confocal micrographs of P-Cap. The nanoparticles' cores are labeled with fluorescein and the oil phases are loaded with Nile red. Scale bars are 20 μm.
Figure 7C:
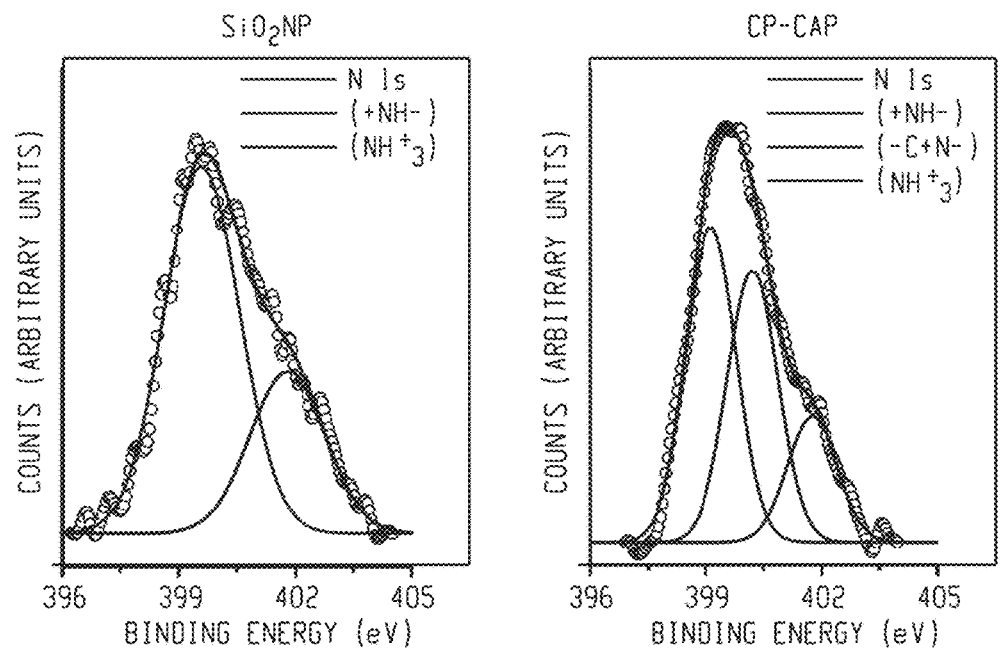
FIG. 7c shows X-ray photoelectron spectra (XPS) showing N 1s core levels arising from $SiO_2$ NPs and CP-Cap.
Figure 7D:
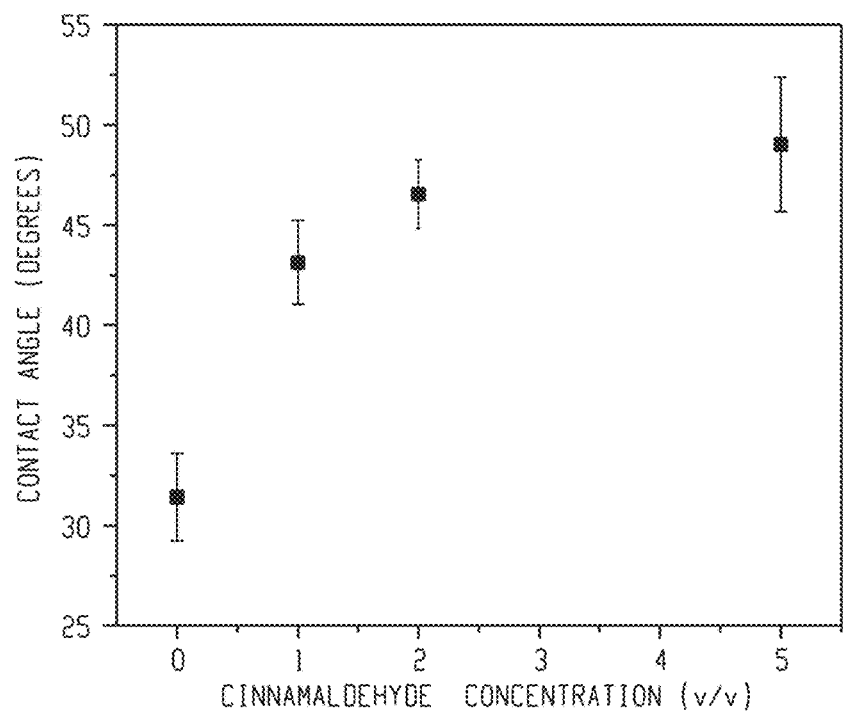
FIG. 7d shows water contact angles of silica nanoparticles following incubation with varying concentrations of cinnamaldehyde.
Figure 8:
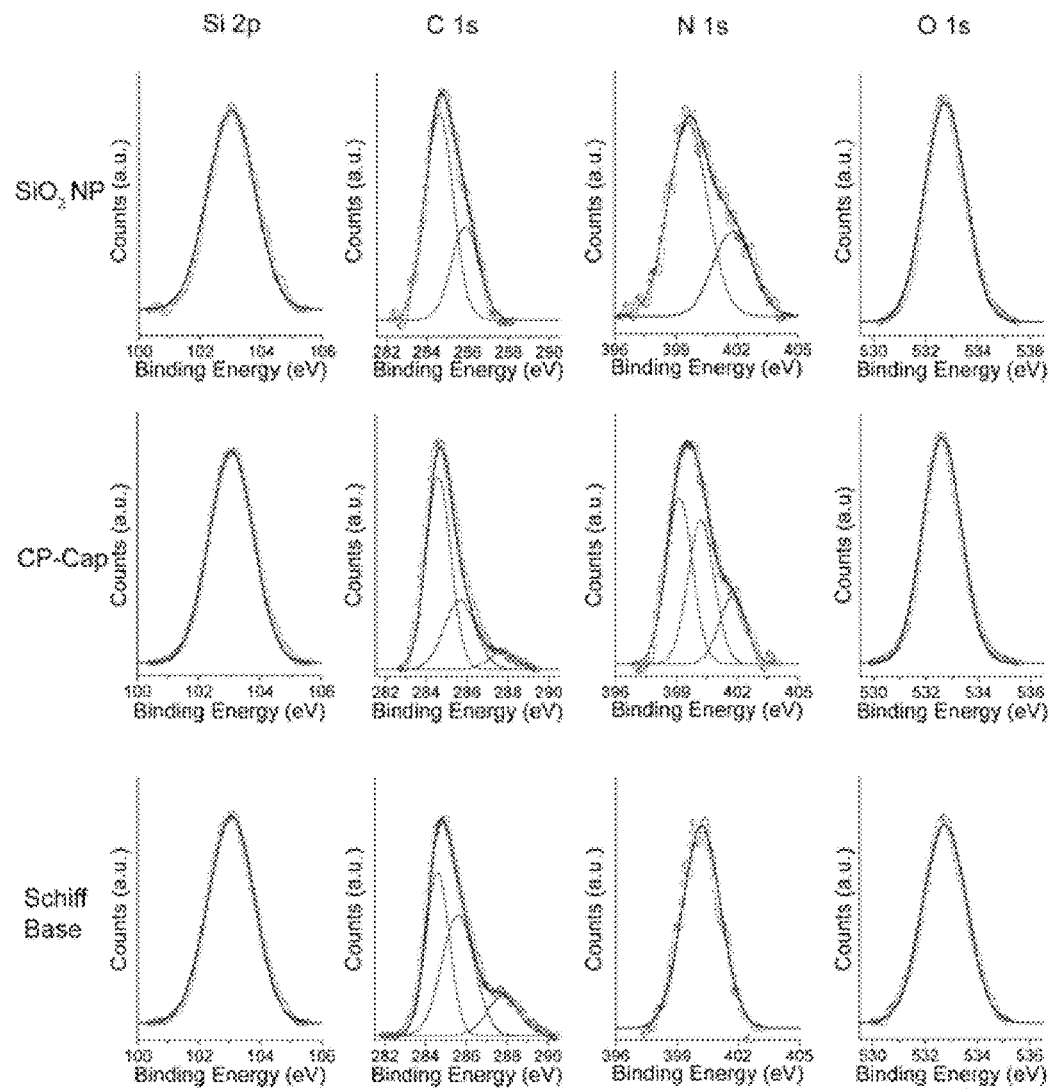
FIG. 8 shows XPS spectra of amino-functionalized $SiO_2$ NPs, CP-Caps, and Schiff base.

Various techniques were used to probe the cinnamaldehyde-nanoparticle interaction, including confocal microscopy, X-ray photoelectron spectroscopy (XPS), attenuated total reflection Fourier transform infrared spectroscopy (ATR-FTIR), and contact angle goniometry. Reactive molecules within the oil core of Pickering emulsions have been previously demonstrated to affect capsule morphologies by modulating the hydrophobicity of the nanoparticles. See, e.g., Duncan, B.; Landis, R. F.; Jerri, H. a; Normand, V.; Benczédi, D.; Ouali, L.; Rotello, V. M. Hybrid Organic-Inorganic Colloidal Composite "Sponges" via Internal Crosslinking. *Small* 2015, 11, 1302-1309; Williams, M.; Warren, N. J.; Fielding, L. A.; Armes, S. P.; Verstraete, P.; Smets, J. Preparation of Double Emulsions Using Hybrid Polymer/Silica Particles: New Pickering Emulsifiers with Adjustable Surface Wettability. *ACS Appl. Mater. Interfaces* 2014, 6, 20919-20927. To determine if structural reorganization occurs with our mixed oil system, capsules were generated using a Nile red loaded oil core and nanoparticles possessing cores labeled with fluorescein isothiocyanate (FITC). As shown in FIG. 7, both capsules with and without cinnamaldehyde possess core-shell morphologies. This result indicates that the 5% v/v loading of cinnamaldehyde into the peppermint oil does not alter the capsule structure XPS and ATR-FTIR were used to elucidate the reactivity of the nanoparticles with the dissolved cinnamaldehyde of the capsules. Prior to analysis, CP-Caps were disrupted with ethanol, centrifuged, and lyophilized to remove any adsorbed cinnamaldehyde. The Schiff base of 3-aminopropyltriethoxysilane and cinnamaldehyde was also synthesized for comparison. As shown in FIG. 7(c), the $SiO_2$ NPs showed two chemically distinct species with a lower binding energy (BE) component at ca. 399.5 eV and a higher BE component at ca. 401.8 eV. These correspond to amine (—NH—) and protonated amine (NH3+) present on the surface of $SiO_2$ NPs that is consistent with previously reported values. See, e.g., Tan, K.; Tan, B.; Kang, E.; Neoh, K. X-Ray Photoelectron Spectroscopy Studies of the Chemical Structure of Polyaniline. *Phys. Rev. B*, 1989, 39, 8070-8073. The N 1s spectra of CP-Cap shows three distinct chemical species. In addition to the two N 1s BE components observed in the SiO2 NPs, a new peak centered at ca. 400.1 eV indicates the formation of an imine functional (—C=N—) group which corroborates well with literature values. See, e.g., Ricci, M.; Trinquecoste, M.; Auguste, F.; Canet, R.; Delhaes, P.; Guimon, C.; Pfister-Guillouzo, G.; Nysten, B.; Issi, J. P. Relationship between the Structural Organization and the Physical Properties of PECVD Nitrogenated Carbons. *J. Mater. Res.*, 1993, 8, 480-488. The N 1s spectra from the synthesized Schiff base (FIG. 8) showed a single chemically distinct N 1s species centered at ca. 400.2 eV, which corresponds to the imine functional group (—C=N—). Similarly, the chemically distinct species of the C 1s spectra obtained from CP-Cap matches well with the synthesized Schiff base further providing evidence on the covalent linkage of the amine and cinnamaldehyde (FIG. 8). Additionally, the Si 2p and O 1s peak shows typical BEs centered at ca. 103.2 eV and 532.6 eV, respectively that matches with reported values for $SiO_2$ NPs. See, e.g., Ramanathan, R.; Campbell, J. L.; Soni, S. K.; Bhargava, S. K.; Bansal, V. Cationic Amino Acids Specific Biomimetic Silicification in Ionic Liquid: A Quest to Understand the Formation of 3-D Structures in Diatoms. *PLoS One* 2011, 6.

Figure 9:
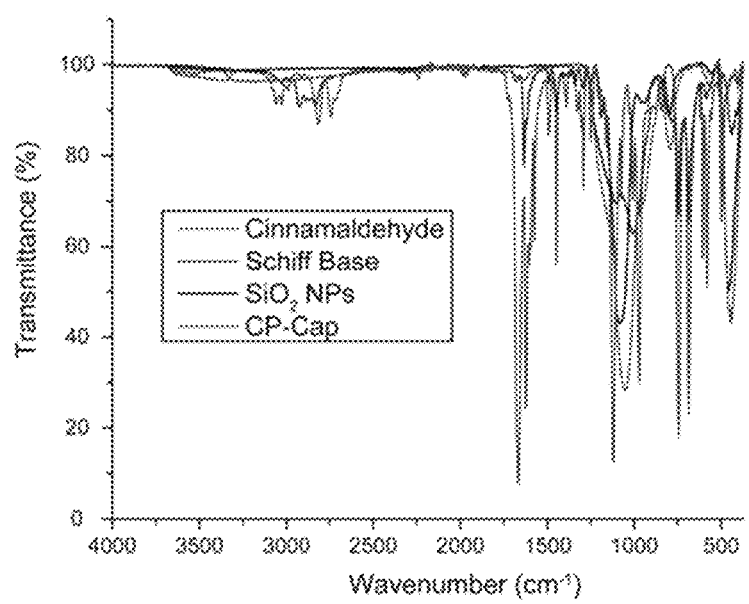
FIG. 9 shows attenuated total reflection Fourier transform infrared spectroscopy (ATR-FTIR) characterization of cinnamaldehyde, the cinnamaldehyde-silane Schiff base, the silica nanoparticles, and CP-Caps after freeze drying.

ATR-FTIR analysis further supported the formation of the cinnamaldehyde Schiff base, as shown in FIG. 9. IR was performed on a Bruker Alpha FTIR spectrophotometer fitted with a platinum ATR QuickSnap sampling module. Cinnamaldehyde was analyzed as a pure liquid. The silica nanoparticles and Schiff base were analyzed as neat solids. The CP-Caps were dissolved in ethanol, sonicated, and centrifuged three times to remove the oil phase. The CP-Cap pellet was then freeze dried in order to obtain a dry solid that was analyzed. Cinnamaldehyde displayed characteristic peaks at 1667 $cm^{-1}$ and 1624 $cm^{-1}$ attributed to the C=O and C=C frequencies. The Schiff base possessed peaks at 1681 $cm^{-1}$ and 1633 $cm^{-1}$ attributed to C=N and C=C bonds, respectively. The Schiff base also displayed peaks at 1102 $cm^{-1}$ and 1006 $cm^{-1}$ attributed to the Si—O and Si—OEt frequencies. Amine-functionalized silica nanoparticles showed characteristic peaks at 1080 $cm^{-1}$ and 947 $cm^{-1}$ attributed to the Si—O and Si—OH frequencies. CP-Caps displayed peaks at frequencies similar to the $SiO_2$ NPs and the Schiff base confirming the formation of the Schiff base complex on the nanoparticles.

Figure 10:
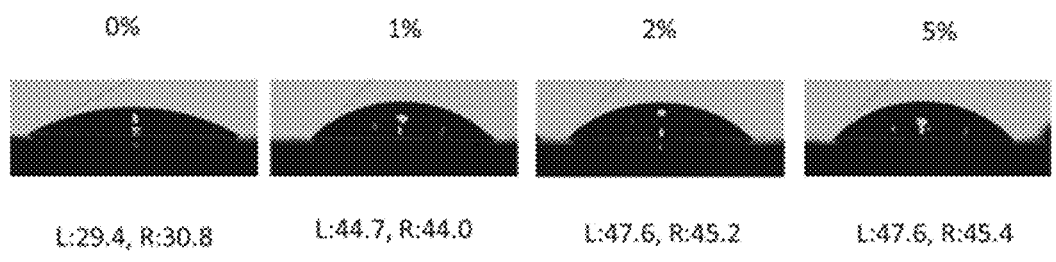
FIG. 10 shows representative digital images of water droplets used to determine contact angles.

An in situ covalent reaction of the primary amine groups on the nanoparticles with cinnamaldehyde should alter the hydrophobicity of the nanoparticle surface improving the stabilization behavior of the Pickering emulsifiers. See, e.g., Pieranski, P. Two-Dimensional Interfacial Colloidal Crystals. *Phys. Rev. Lett.* 1980, 45, 569-572. Contact angle goniometry was used to measure the change in nanoparticle hydrophobicity, as shown in FIG. 10. Nanoparticles were deposited onto silicon wafers and briefly incubated in dichloromethane solutions with varying amounts of dissolved cinnamaldehyde. The surfaces were then rinsed with dichloromethane, dried, and the water contact angles were obtained. FIG. 10 shows that as the percentage of cinnamaldehyde by volume increases from 0% to 5% %, the water contact angle of the nanoparticles increases from 31° to 49°. This increase in water contact angle, taken together with the XPS data, the ATR-FTIR data, and confocal images, indicates that the inclusion of cinnamaldehyde within the peppermint oil core generates a distinct, multi-component capsule structure.

Figure 11:
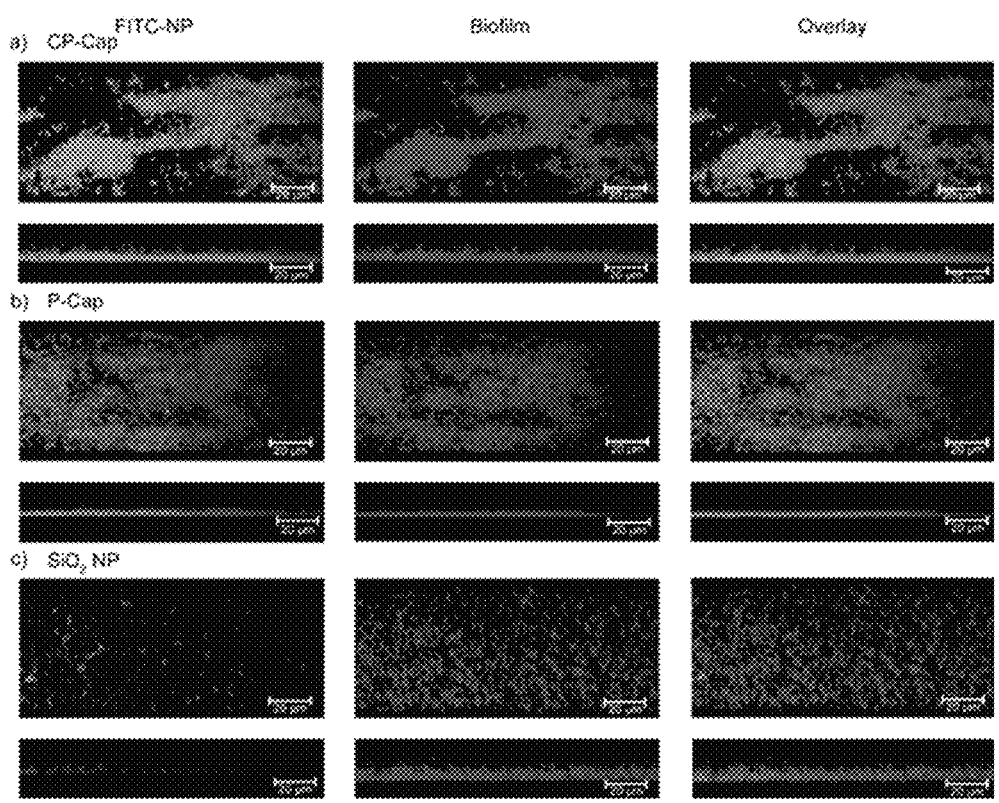
FIG. 11 shows representative 3D projections of confocal image stacks of 1 day-old *E. coli* DH5α biofilm after 3 hrs treatment with a) CP-Cap containing FITC-labeled SiO2 NP, b) P-Cap containing FITC-labeled $SiO_2$ NP, and c) FITC-labeled $SiO_2$ NP at 20% (v/v % of 2% emulsion) concentration. Upper panels are projection at 247° angle turning along Y axis and lower panels are at 270° angle turning along Y axis. Scale bars are 20 μm.

Biofilms produce extracellular polymeric substances that prevent effective delivery of therapeutics. See, e.g., Hurdle, J. G.; O'Neill, A. J.; Chopra, I.; Lee, R. E. Targeting Bacterial Membrane Function: An Underexploited Mechanism for Treating Persistent Infections. *Nat. Rev. Microbiol.* 2011, 9, 62-75. Having established that the capsules have core-shell morphologies and the cinnamaldehyde is successfully incorporated into the capsules, we set out to determine whether these capsules could effectively penetrate into biofilms. Using fluorescently labeled nanoparticles to track the delivery of the emulsions, we treated biofilms from *E. coli* that had been modified to express E2-Crimson, a far-red fluorescent protein. As shown in FIG. 11, both P-Cap and CP-Cap diffuse into the biofilm matrix and efficiently disperse throughout the biofilm whereas the unassembled nanoparticles displayed minimal penetration. These data indicate the capsules deliver their payload in a burst release fashion and that both the oil core and nanoparticle shell are operative for effective delivery.

Next, we investigated the therapeutic behavior of the capsules against established bacterial biofilms. One laboratory strain, *E. coli* DH5α, and 3 pathogenic bacteria strains of clinical isolates, *P. aeruginosa* (CD-1006), *S. aureus* (CD-489, a methicillin-resistant strain), and *E. cloacae* complex (CD-1412), were chosen to test our system. As shown in FIG. 12, both the CP-Cap and P-Cap vehicles effectively were able to kill bacteria cells in all four biofilms, with CP-Cap possessing greater activity. The capsules demonstrated a dramatically enhanced efficacy compared with the unencapsulated oil, supporting the hypothesis that the cationic nanoparticle shell of the capsules increases interaction with the biofilms. See, e.g., Li, X.; Yeh, Y.; Giri, K.; Mout, R.; Landis, R. F.; Prakash, Y. S.; Rotello, V. M. Control of Nanoparticle Penetration into Biofilms through Surface Design. *Chem. Commun. (Camb).* 2015, 51, 282-285. In addition, the acidic pH of the biofilm environment should promote the hydrolysis of Schiff bases, enhancing the sustained release of cinnamaldehyde. See, e.g., Harrison, J. J.; Ceri, H.; Turner, R. J. Multimetal Resistance and Tolerance in Microbial Biofilms. *Nat. Rev. Microbiol.* 2007, 5, 928-938. These capsules were able to treat both Gram negative (*E. coli, P. aeruginosa*, and *E. cloacae* complex) and Gram positive (*S. aureus*) bacteria. Notably, the capsules demonstrated a similar efficacy against the multi-drug resistant *S. aureus* stain when compared to the non-resistant strains, supporting that these capsules present a viable treatment alternative to traditional antibiotics.

Biofilm infections within wounds interfere with the ability of the host to regenerate damaged tissue. See, e.g., Roy, S.; Elgharably, H.; Sinha, M.; Ganesh, K.; Chaney, S.; Mann, E.; Miller, C.; Khanna, S.; Bergdall, V. K.; Powell, H. M.; et al. Mixed-Species Biofilm Compromises Wound Healing by Disrupting Epidermal Barrier Function. *J. Pathol.* 2014, 233, 331-343. Fibroblasts in particular play a vital role in the wound healing process, helping to close the injury and redevelop the extracellular matrix within the skin. See, e.g., Watt, F. M. Mammalian Skin Cell Biology: At the Interface between Laboratory and Clinic. *Science* 2014, 346, 937-940; Sun, B. K.; Siprashvili, Z.; Khavari, P. A. Advances in Skin Grafting and Treatment of Cutaneous Wounds. *Science* 2014, 346, 941-945. We used an in vitro co-culture model comprised of mammalian fibroblasts and a biofilm to determine whether our capsules could successfully treat a biofilm in the presence of host cells. See, e.g., Li, X.; Kong, H.; Mout, R.; Saha, K.; Moyano, D. F.; Robinson, S. M.; Rana, S.; Zhang, X.; Riley, M. A.; Rotello, V. M. Rapid Identification of Bacterial Biofilms and Biofilm Wound Models Using a Multichannel Nanosensor. *ACS Nano* 2014, 8, 12014-12019. *E. coli* DH5α bacteria were seeded with a confluent NIH 3T3 fibroblast cell monolayer overnight to generate biofilms prior to treatment. The co-cultures were treated with capsules for 3 hours, washed, and the viabilities of both fibroblasts and bacteria were measured. As shown in FIG. 13, CP-Cap effectively treated the biofilm infection whereas P-Cap and the controls did not. The capsule structure also prevented the toxic effects shown by the unencapsulated peppermint oil to the fibroblasts. Notably, CP-Cap enhanced 3T3 cell growth in agreement with studies that cinnamaldehyde can promote insulin-like growth factor-I signaling, increasing cell proliferation. See, e.g., Takasao, N.; Tsuji-Naito, K.; Ishikura, S.; Tamura, A.; Akagawa, M. Cinnamon Extract Promotes Type I Collagen Biosynthesis via Activation of IGF-I Signaling in Human Dermal Fibroblasts. *J. Agric. Food Chem.* 2012, 60, 1193-1200.

Experimental Details Follow.

Materials. All reagents/materials were purchased from Fisher Scientific and used as received. Boron-doped Si wafers were purchased from WRS Materials. NIH-3T3 cells (ATCC CRL-1658) were purchased from ATCC. Dulbecco's Modified Eagle's Medium (DMEM) (DMEM; ATCC 30-2002) and fetal bovine serum (Fisher Scientific, SH3007103) were used in cell culture. Pierce LDH Cytotoxicity Assay Kit was purchased from Fisher Scientific.

Silica nanoparticles were synthesized according to the reported procedure. See, e.g., Duncan, B.; Landis, R. F.; Jerri, H. A; Normand, V.; Benczédi, D.; Ouali, L.; Rotello, V. M. Hybrid Organic-Inorganic Colloidal Composite "Sponges" via Internal Crosslinking. *Small* 2015, 11, 1302-1309; Stöber, W.; Fink, A.; Bohn, E. Controlled Growth of Monodisperse Silica Spheres in the Micron Size Range. *J. Colloid Interface Sci.* 1968, 26, 62-69. Briefly, to synthesize 150 nanometer amine-functionalized silica nanoparticles, 24 milliliters of ammonium hydroxide were added to 300 milliliters of absolute ethanol and stirred for five minutes in a 500 milliliters round-bottom flask. Then 12 milliliters of tetraethyl orthosilicate were added to the reaction flask and stirred overnight at room temperature. To functionalize the surface of the nanoparticles, 1.22 milliliters of 3-aminopropyl triethoxysilane were added and the reaction was stirred for an additional 24 hours. The nanoparticles were purified by centrifuging and re-dispersing in water and ethanol (3 times each).

Synthesis of fluorescein labeled nanoparticles (Santra, S.; Liesenfeld, B.; Bertolino, C.; Dutta, D.; Cao, Z.; Tan, W.; Moudgil, B. M.; Mericle, R. A. Fluorescence Lifetime Measurements to Determine the Core—shell Nanostructure of FITC-Doped Silica Nanoparticles: An Optical Approach to Evaluate Nanoparticle Photostability. *J. Lumin.* 2006, 117, 75-82) was performed following a similar method wherein 5.25 milligrams of fluorescein isothiocyanate were reacted with 69.0 milligrams of 3-aminopropyl triethoxysilane in one milliliter of absolute ethanol under nitrogen overnight. This fluorescent conjugate mixture was added to the nanoparticle reaction solution 5 minutes after the addition of tetraethyl orthosilicate. The procedure then proceeded as described above.

Stock capsules solutions were prepared in 1.5 milliliter Eppendorf tubes. To prepare the stock P-Cap emulsions, 300 microliters (µL) of peppermint oil was added to 1.2 milliliters of a 1.2% wt. solution of $SiO_2$ NPs in MilliQ $H_2O$ adjusted to pH 10 and was emulsified in an amalgamator for 50 seconds. To prepare the stock CP-Cap emulsions, 15 µL of cinnamaldehyde was dissolved in 285 µL of peppermint oil prior to emulsification as described. The emulsions were allowed to rest overnight prior to use.

X-ray photoelectron spectroscopy (XPS) samples were prepared by drop-casting the sample on a 100 nanometer gold-coated silicon substrate. XPS measurements were carried out using Physical Electronics Quantum 2000 spectrometer at a pressure below $1 \times 10^{-9}$ Torr. The survey scan, C 1s, N 1s, O 1s and Si 2p core level spectra for all samples were recorded with un-monochromatized Al Kα radiation (photon energy of 1486.6 eV) at a pass energy of 46.95 eV and electron takeoff angle of 15°. The overall resolution was 0.2 eV for the XPS measurements. Chemically distinct species were resolved using a Gaussian-Lorentzian function with non-linear least-square fitting procedure. All XPS spectra were background corrected using the Shirley algorithm and aligning the elemental binding energies to the adventitious carbon (C1s) binding energy of 284.6 eV.

Contact angle goniometry samples were prepared by immersing a clean silicon wafer (1 centimeter×1 centimeter) into 1 milliliter of a 1.2% wt. solution of $SiO_2$ NPs in MilliQ $H_2O$ adjusted to pH 10 for 5 minutes. Wafers were then washed with MilliQ $H_2O$ to removed excess nanoparticles and dried under a $N_2$ stream. Samples were then incubated in 1 milliliter solutions of dichloromethane with varying amounts (0, 1, 2, 5 volume percent) of dissolved cinnamaldehyde for 5 minutes. Wafers were then washed with dichloromethane and dried under a nitrogen stream. Static water contact angles were measured using a VCA Optima surface analysis/goniometry system with water droplets size of 2 µL.

Biofilm Formation

Biofilms were grown as previously reported. See, e.g., Li, X.; Kong, H.; Mout, R.; Saha, K.; Moyano, D. F.; Robinson, S. M.; Rana, S.; Zhang, X.; Riley, M. A.; Rotello, V. M. Rapid Identification of Bacterial Biofilms and Biofilm Wound Models Using a Multichannel Nanosensor. *ACS Nano* 2014, 8, 12014-12019. Bacteria were inoculated in lysogeny broth (LB) medium at 37° C. until stationary phase. The cultures were then harvested by centrifugation and washed with 0.85% sodium chloride solution three times. Concentrations of resuspended bacterial solution were determined by optical density measured at 600 nm. LB medium was supplemented with 0.1% glucose, 1 mM magnesium sulfate, 0.15 M ammonium sulfate, and 34 mM citrate and buffered to pH 7 to ensure bacterial adherence to the microplate. Seeding solutions were then made in this modified LB medium to reach an $OD_{600}$ of 0.1. A 100 µL amount of the seeding solutions was added to each well of the 96 well microplate. The plates were covered and incubated at room temperature under static conditions for 1 day.

A 2 volume percent emulsion stock solution was made by diluting the generated capsules into LB medium. The stock solution was then diluted to the desired level and incubated with the biofilms for 3 hours. Biofilms were washed with phosphate buffer saline (PBS) three times and viability was determined using an Alamar Blue assay. See, e.g., Margarida Pereira, A.; Cristina Abreu, A.; Simões, M. Action of Kanamycin Against Single and Dual Species Biofilms of *Escherichia Coli* and *Staphylococcus Aureus*. *J. Microbiol. Res.* 2012, 2, 84-88. Modified LB medium without bacteria was used as a negative control.

Biofilm-3T3 Fibroblast Cell Co-Culture

Co-culture was performed as previously described. See, e.g., Takasao, N.; Tsuji-Naito, K.; Ishikura, S.; Tamura, A.; Akagawa, M. Cinnamon Extract Promotes Type I Collagen Biosynthesis via Activation of IGF-I Signaling in Human Dermal Fibroblasts. *J. Agric. Food Chem.* 2012, 60, 1193-1200. Briefly, a total of 20,000 NIH 3T3 (ATCC CRL-1658) cells were cultured in Dulbecco's modified Eagle medium (DMEM; ATCC 30-2002) with 10% bovine calf serum and 1% antibiotics at 37° C. in a humidified atmosphere of 5% $CO_2$. Cells were kept for 24 h to reach a confluent monolayer. Bacteria were inoculated and harvested as described above, and seeding solutions were made in buffered DMEM supplemented with glucose to reach an $OD_{600}$ of 0.1. Old medium was removed from 3T3 cells followed by addition of 100 μL of seeding solution. The co-cultures were then stored in a box with damp paper towels at 37° C. overnight without shaking.

Testing solutions at different concentrations were made by diluting capsules into DMEM prior to use. Media was removed from co-culture, replaced with testing solutions, and incubated for 3 hours at 37° C. Co-cultures were then analyzed using a LDH cytotoxicity assay to determine mammalian cell viability according the manufacturer's instructions. See, e.g., Decker, T.; Lohmann-Matthes, M. L. A Quick and Simple Method for the Quantitation of Lactate Dehydrogenase Release in Measurements of Cellular Cytotoxicity and Tumor Necrosis Factor (TNF) Activity. *J. Immunol. Methods* 1988, 115, 61-69. To determine bacteria viability in biofilms, the testing solutions were removed and co-cultures were washed with PBS. Fresh PBS was then added to disperse remaining bacteria from biofilms in co-culture by sonication for 20 minutes and mixing with pipette. The solutions containing dispersed bacteria were then plated onto agar plates and colony forming units were counted after incubation at 37° C. overnight.

The microcapsules, dispersions and methods of the present disclosure include at least the following embodiments.

Embodiment 1

A stabilized microcapsule comprising a liquid hydrophobic core comprising an essential oil and an aromatic monoaldehyde; and a shell encapsulating the core, the shell comprising a plurality of amino-functionalized inorganic nanoparticles.

Embodiment 1a

A stabilized microcapsule comprising, a liquid hydrophobic core comprising an essential oil; and a shell encapsulating the core, the shell comprising a plurality of amino-functionalized inorganic nanoparticles, wherein the amino-functionalized inorganic nanoparticles further comprise a reaction product formed from reaction of an amino-functionalized inorganic nanoparticle and an aromatic monoaldehyde covalently bound to a surface of the nanoparticle.

Embodiment 2

The microcapsule of embodiment 1 or 1a, wherein the inorganic nanoparticles are metal nanoparticles, metal oxide nanoparticles, or a combination thereof, and wherein the nanoparticles have one or more dimensions of less than 1000 nanometers.

Embodiment 3

The microcapsule of any of embodiments 1 to 2, wherein the inorganic nanoparticles comprise silica, titanium dioxide, or a combination thereof.

Embodiment 4

The microcapsule of any of embodiments 1 to 3, wherein the inorganic nanoparticles comprise silica.

Embodiment 5

The microcapsule of any of embodiments 1 to 4, wherein the inorganic nanoparticles have an average diameter of 100 to 250 nanometers.

Embodiment 6

The microcapsule of any of embodiments 1 to 5, wherein the essential oil is selected from the group consisting of peppermint oil, oregano oil, thymol, menthol, methyl salicylate, eucalyptol, carvacrol, camphor, anethole, carvone, eugenol, isoeugenol, limonene, osimen, n-decyl alcohol, citronel, a-salpineol, methyl acetate, citronellyl acetate, methyl eugenol, cineol, linalool, ethyl linalaol, safrola vanillin, spearmint oil, lemon oil, orange oil, sage oil, rosemary oil, cinnamon oil, pimento oil, laurel oil, cedar leaf oil, clove oil, cilantro oil, coriander oil, or a combination thereof.

Embodiment 7

The microcapsule of any of embodiments 1 to 6, wherein the essential oil comprises peppermint oil.

Embodiment 8

The microcapsule of any of embodiments 1 to 7, wherein the aromatic monoaldehyde is cinnamaldehyde.

Embodiment 9

The microcapsule of any of embodiments 1 to 8, wherein the amino-functionalized inorganic nanoparticles further comprise a reaction product covalently bound to a surface of the nanoparticle, wherein the reaction product is formed from reaction of an amino-functionalized inorganic nanoparticle and one or more aromatic monoaldehydes.

Embodiment 10

The microcapsule of any of embodiments 1 to 9, comprising 0.01 to 10 volume percent of the aromatic monoaldehyde, based on the total volume of the essential oil and the aromatic monoaldehyde.

Embodiment 11

The microcapsule of any of embodiments 1 to 10, comprising 1 to 10 weight percent of the inorganic nanoparticles, based on the total weight of the microcapsule.

Embodiment 12

The microcapsule of any of embodiments 1 to 11, wherein the microcapsule has an average diameter of 1 to 20 micrometers.

Embodiment 13

The microcapsule of any of embodiments 1 to 12, wherein the essential oil comprises peppermint oil; the aromatic monoaldehyde is cinnamaldehyde; the microcapsule comprises 1 to 5 volume percent cinnamaldehyde, based on the total volume of the essential oil and the aromatic monoaldehyde; the inorganic nanoparticles are silica nanoparticles having an average diameter of 140 to 160 nanometers; and the microcapsule has an average diameter of 4 to 9 micrometers.

Embodiment 14

The microcapsule of any of embodiments 1 to 13, comprising, based on the total weight of the microcapsule, 90 to 99 weight percent of the liquid hydrophobic core; and 1 to 10 weight percent of a shell encapsulating the core; wherein the liquid hydrophobic core comprises, based on the total weight of the core, 90 to 99 weight percent peppermint oil; and 1 to 10 weight percent cinnamaldehyde.

Embodiment 15

A dispersion comprising a plurality of stabilized microcapsules according to any of embodiments 1 to 14.

Embodiment 16

The dispersion of embodiment 15, wherein the stabilized microcapsules are dispersed in an aqueous solution.

Embodiment 17

The dispersion of embodiment 15 or 16, wherein each microcapsule comprises a shell comprising silica nanoparticles; and the silica is present in an amount of less than or equal to 3 weight percent, based on the total weight of the dispersion.

Embodiment 18

A method of treating a bacterial biofilm, the method comprising, contacting the dispersion of any of embodiments 15 to 17 with a bacterial biofilm.

Embodiment 19

The method of embodiment 18, wherein the bacterial biofilm comprises *Escherichia coli, Pseudomonas* bacteria, *Staphylococcal* bacteria, Enterobacteriaceae bacteria, *Streptococcus* bacteria, *Haemophilus influenzae, Leptospira interrogans, Legionella* bacteria, or a combination thereof.

Embodiment 20

The method of embodiment 18 or 19, wherein the contacting is in the presence of a host cell, wherein the dispersion is non-toxic to the host cell.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

All cited patents, patent applications, and other references are incorporated herein by reference in their entirety, including priority U.S. Patent Application No. 62/208,114, filed Aug. 21, 2015. However, if a term in the present application contradicts or conflicts with a term in the incorporated reference, the term from the present application takes precedence over the conflicting term from the incorporated reference.

All ranges disclosed herein are inclusive of the endpoints, and the endpoints are independently combinable with each other. Each range disclosed herein constitutes a disclosure of any point or sub-range lying within the disclosed range. "Or" means "and/or". "Combination" is inclusive of blends, mixtures, alloys, reaction products, and the like.

The use of the terms "a" and "an" and "the" and similar referents in the context of describing the invention (especially in the context of the following claims) are to be construed to cover both the singular and the plural, unless otherwise indicated herein or clearly contradicted by context. Further, it should further be noted that the terms "first," "second," and the like herein do not denote any order, quantity, or importance, but rather are used to distinguish one element from another.

The invention claimed is:
1. A stabilized microcapsule comprising,
a single liquid hydrophobic core comprising an essential oil and an aromatic monoaldehyde; and
a single shell encapsulating the core, the shell consisting of a plurality of amino-functionalized inorganic nanoparticles having
one or more amino functional groups directly covalently bound to the surface of the inorganic nanoparticles;
one or more amino functional groups covalently bound to the surface of the inorganic nanoparticles by a linker comprising a $C_{1-12}$ alkyl group, a $C_{6-20}$ aryl group, or an alkylene oxide group between the amino functional group and the surface;
or combination thereof;
wherein the essential oil is selected from the group consisting of peppermint oil, oregano oil, thymol, menthol, methyl salicylate, eucalyptol, carvacrol, camphor, anethole, carvone, eugenol, isoeugenol, osimen, n-decyl alcohol, citronel, a-salpineol, methyl acetate, citronellyl acetate, methyl eugenol, cineol, ethyl linalaol, safrola vanillin, spearmint oil, lemon oil, orange oil, sage oil, rosemary oil, cinnamon oil, pimento oil, laurel oil, cedar leaf oil, clove oil, cilantro oil, coriander oil, and a combination thereof;
and wherein the aromatic monoaldehyde is cinnamaldehyde.
2. A stabilized microcapsule comprising,
a single liquid hydrophobic core comprising an essential oil and an aromatic monoaldehyde; and
a single shell encapsulating the core, the shell consisting of a plurality of functionalized inorganic nanoparticles having
one or more amino functional groups directly covalently bound to the surface of the inorganic nanoparticles;
one or more amino functional groups covalently bound to the surface of the inorganic nanoparticles by a linker comprising a $C_{1-12}$ alkyl group, a $C_{6-20}$ aryl group, or an alkylene oxide group between the amino functional group and the surface;
a reaction product formed from reaction of an amino-functionalized inorganic nanoparticle and the aromatic monoaldehyde,
or a combination thereof;
wherein the essential oil is selected from the group consisting of peppermint oil, oregano oil, thymol, menthol, methyl salicylate, eucalyptol, carvacrol, camphor, anethole, carvone, eugenol, isoeugenol, osimen, n-decyl alcohol, citronel, a-salpineol, methyl acetate, citronellyl acetate, methyl eugenol, cineol, ethyl linalaol, safrola vanillin, spearmint oil, lemon oil, orange oil, sage oil, rosemary oil, cinnamon oil, pimento oil, laurel oil, cedar leaf oil, clove oil, cilantro oil, coriander oil, and a combination thereof;

and wherein the aromatic monoaldehyde is cinnamaldehyde.

3. The microcapsule of claim 1, wherein the inorganic nanoparticles are metal nanoparticles, metal oxide nanoparticles, or a combination thereof, and wherein the nanoparticles have one or more dimensions of less than 1000 nanometers.

4. The microcapsule of claim 1, wherein the inorganic nanoparticles comprise silica, titanium dioxide, or a combination thereof.

5. The microcapsule of claim 1, wherein the inorganic nanoparticles have an average diameter of 100 to 250 nanometers.

6. The microcapsule of claim 1, wherein the essential oil comprises peppermint oil.

7. The microcapsule of claim 1, comprising 0.01 to 10 volume percent of the aromatic monoaldehyde, based on the total volume of the essential oil and the aromatic monoaldehyde.

8. The microcapsule of claim 1, comprising 1 to 10 weight percent of the inorganic nanoparticles, based on the total weight of the microcapsule.

9. The microcapsule of claim 1, wherein the microcapsule has an average diameter of 1 to 20 micrometers.

10. The microcapsule of claim 1, wherein
the essential oil comprises peppermint oil;
the aromatic monoaldehyde is cinnamaldehyde;
the microcapsule comprises 1 to 5 volume percent cinnamaldehyde, based on the total volume of the essential oil and the aromatic monoaldehyde;
the inorganic nanoparticles are silica nanoparticles having an average diameter of 140 to 160 nanometers; and the microcapsule has an average diameter of 4 to 9 micrometers.

11. The microcapsule of claim 1, comprising, based on the total weight of the microcapsule,
90 to 99 weight percent of the liquid hydrophobic core; and
1 to 10 weight percent of the shell encapsulating the core; wherein
the liquid hydrophobic core comprises, based on the total weight of the core,
90 to 99 weight percent peppermint oil; and
1 to 10 weight percent cinnamaldehyde.

12. A method of treating a bacterial biofilm the method comprising,
contacting a dispersion comprising a plurality of the stabilized microcapsule according to claim 1 with a bacterial biofilm.

13. The method of claim 12, wherein the stabilized microcapsules are dispersed in an aqueous solution.

14. The method of claim 12, wherein
each microcapsule comprises a shell consisting of silica nanoparticles; and
the silica is present in an amount of less than or equal to 3 weight percent, based on the total weight of the dispersion.

15. The method of claim 12, wherein the bacterial biofilm comprises *Escherichia coli, Pseudomonas* bacteria, Staphylococcal bacteria, Enterobacteriaceae bacteria, *Streptococcus* bacteria, *Haemophilus influenzae, Leptospira interrogans, Legionella* bacteria, or a combination thereof.

16. The method of claim 12, wherein the contacting is in the presence of a host cell, wherein the dispersion is non-toxic to the host cell.

* * * * *